US006479534B1

(12) United States Patent
Bentley et al.

(10) Patent No.: US 6,479,534 B1
(45) Date of Patent: Nov. 12, 2002

(54) INDOLINE DERIVATIVES AND METHOD OF TREATING OBESITY

(76) Inventors: Jonathan Mark Bentley, Oakdene Court, 613 Reading Court, Winnersh, Wokingham RG41 5UA (GB); James Edward Paul Davidson, Oakdene Court, 613 Reading Court, Winnersh, Wokingham RG41 5UA (GB); Howard Langham Mansell, Oakdene Court, 613 Reading Court, Winnersh, Wokingham RG41 5UA (GB); Nathaniel Julius Thomas Monck, Oakdene Court, 613 Reading Court, Winnersh, Wokingham RG41 5UA (GB)

( * ) Notice: Subject to any disclaimer, the term of this patent is extended or adjusted under 35 U.S.C. 154(b) by 0 days.

(21) Appl. No.: 09/977,783

(22) Filed: Oct. 15, 2001

(30) Foreign Application Priority Data

Oct. 16, 2000 (EP) ............................. 00122539

(51) Int. Cl.⁷ ..................... A61K 31/40; C07D 209/82
(52) U.S. Cl. ...................... 514/411; 548/449
(58) Field of Search ................. 548/449, 432, 548/430, 429; 514/411

(56) References Cited

U.S. PATENT DOCUMENTS

| 2,541,211 A | | 2/1951 | Cusic et al. |
| 2,687,414 A | | 8/1954 | Cusic et al. |
| 3,142,678 A | | 7/1964 | Rice et al. |
| 3,663,567 A | * | 5/1972 | Eberle ................ 548/449 |
| 3,931,222 A | * | 1/1976 | Cross et al. ........... 548/449 |
| 4,598,089 A | | 7/1986 | Hadvary et al. |
| 6,004,996 A | | 12/1999 | Shah et al. |

FOREIGN PATENT DOCUMENTS

| DE | 930 988 | 7/1955 |
| DE | 24 38 413 | 3/1975 |
| EP | 185 359 | 6/1986 |
| EP | 189 577 | 8/1986 |
| EP | 443 449 | 8/1991 |
| EP | 524 495 | 1/1993 |
| EP | 655 440 | 5/1995 |
| FR | 2242983 | 12/1975 |
| WO | WO 99/34786 | 7/1998 |
| WO | WO 98/30548 | 7/1999 |
| WO | WO 00/09122 | 2/2000 |
| WO | WO 00/09123 | 2/2000 |

OTHER PUBLICATIONS

Parker, "Obesity: Trends and Treatments", Scrip Reports, PJB Publications Limited, (1996).
Kennett et al., Psychopharmacology, 96, pp. 93–100 (1988).
Kennett et al., Eur. J. Pharmacol., 141, pp. 429–435 (1987).
Kitchener et al., Psychopharmacology, 113, pp. 369–377 (1994).
Walsh et al., Psychopharmacology, 116, pp. 120–122 (1994).
Sargeant et al., Psychopharmacology, 133, pp. 309–312 (1997).
Tecott et al., Nature, vol. 374, pp. 542–546 (1995).
Kennett et al., Neuropharmacology, vol. 36, pp. 609–620, (1997).
Khim. Geterotskikl. Soedin, No. 3, pp. 371–376 (1970).
Hoyer et al., European J. Pharmacology, 118, pp. 13–23 (1985).
Schmuck et al., FEBS Letters, 342, pp. 85–90 (1994).
McKenna et al., J. Neuroscience, 9, pp. 3482–3490 (1989).
Abstract CA 2132887.
Abstract CA 2153937.
J. Med. Chem., 13, pp. 327–328 (1970).
J. Med. Chem., 16, pp. 1411–1415 (1973).
J. Med. Chem., 7, pp. 623–625 (1964).
Rice et al., J. Med. Chem., 7(3), pp. 313–319 (1964).

* cited by examiner

Primary Examiner—Robert W. Ramsuer
Assistant Examiner—Rebecca Anderson

(57) ABSTRACT

The present invention relates to indoline derivatives. These compounds are especially useful for the prevention and treatment of disorders of the central nervous system; damage to the central nervous system; cardiovascular disorders; gastrointestinal disorders; diabetes, sleep apnea, and especially for the treatment and prevention of obesity.

32 Claims, No Drawings

INDOLINE DERIVATIVES AND METHOD OF TREATING OBESITY

FIELD OF THE INVENTION

The present invention relates to indoline derivatives, to processes and intermediates for their preparation, to pharmaceutical compositions comprising them and to their medicinal use. The active compounds of the present invention are useful in treating obesity, diabetes and other disorders.

BACKGROUND OF THE INVENTION

It has been recognised that obesity is a disease process influenced by environmental factors in which the traditional weight loss methods of dieting and exercise need to be supplemented by therapeutic products (S. Parker, "Obesity: Trends and Treatments", Scrip Reports, PJB Publications Ltd, 1996).

Whether someone is classified as overweight or obese is generally determined on the basis of their body mass index (BMI) which is calculated by dividing body weight (kg) by height squared ($m^2$). Thus, the units of BMI are $kg/m^2$ and it is possible to calculate the BMI range associated with minimum mortality in each decade of life. Overweight is defined as a BMI in the range 25–30 $kg/m^2$, and obesity as a BMI greater than 30 $kg/m^2$. There are problems with this definition in that it does not take into account the proportion of body mass that is muscle in relation to fat (adipose tissue). To account for this, obesity can also be defined on the basis of body fat content: greater than 25% and 30% in males and females, respectively.

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (XENICAL®) and Sibutramine. Orlistat (a lipase inhibitor) inhibits fat absorption directly and tends to produce a high incidence of unpleasant (though relatively harmless) side-effects such as diarrhoea. Sibutramine (a mixed 5-HT/noradrenaline reuptake inhibitor) can increase blood pressure and heart rate in some patients. The serotonin releaser/reuptake inhibitors fenfluramine (Pondimin®) and dexfenfluramine (Redux®) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

The non-selective $5\text{-HT}_{2C}$ receptor agonists/partial agonists m-chlorphenylpiperazine (mCPP) and trifluoromethylphenylpiperazine (TFMPP) have been shown to reduce food intake in rats (G. A. Kennett and G. Curzon, Psychopharmacol., 1988, 98, 93–100; G. A. Kennett, C. T. Dourish and G. Curzon, Eur. J. Pharmacol, 1987, 141, 429–453) and to accelerate the appearance of the behavioural satiety sequence (S. J. Kitchener and C. T. Dourish, Psychopharmacol., 1994, 113, 369–377). Recent findings from studies with mCPP in normal human volunteers and obese subjects have also shown decreases in food intake. Thus, a single injection of mCPP decreased food intake in female volunteers (A. E. S. Walsh et al, Psychopharmacol., 1994, 116, 120–122) and decreased the appetite and body weight of obese male and female subjects during subchronic treatment for a 14 day period (P. A. Sargeant et al, Psychopharmacol, 1997, 113, 309–312). The anorectic action of mCPP is absent in $5\text{-HT}_{2C}$ receptor knockout mutant mice (L. H. Tecott et al., Nature, 1995, 374, 542–546) and is antagonised by $5\text{-HT}_{2C}$ receptor antagonist SB-242084 in rats (G. A. Kennett et al, Neuropharmacol., 1997, 36, 609–620). It seems therefore that mCPP decreases food intake via an agonist action at the $5\text{-HT}_{2C}$ receptor.

Other compounds which have been proposed as $5\text{-HT}_{2C}$ receptor agonists for use in the treatment of obesity include the substituted 1-aminoethyl indoles disclosed in EP-A-0655440. CA-2132887 and CA-2153937 disclose that tricyclic 1-aminoethylpyrrole derivatives and tricyclic 1-aminoethyl pyrazole derivatives bind to $5\text{-HT}_{2C}$ receptors and may be used in the treatment of obesity. WO-A-98/30548 discloses aminoalkylindazole compounds as $5\text{-HT}_{2C}$-agonists for the treatment of CNS diseases and appetite regulation disorders. Substituted 1,2,3,4-tetrahydrocarbazoles have been reported as synthetic trypanocides in J. Med. Chem., 1970, 13, 327 and J. Med. Chem., 1973, 16, 1411. 9-(2-Dialkylaminopropyl)-1,2,3,4-tetrahydrocarbazoles have been disclosed in U.S. Pat. Nos. 2,687,414 and 2,541,211. 7-Substituted-9-(2-dialkylaminoethyl)-1,2,3,4-tetrahydrocarbazoles have been disclosed in DE 930,988. The pharmacological effects of 2,3-polymethyleneindoles have been described in J. Med. Chem., 1964, 69, 2910. Derivatives of polynuclear indoles have been described as antidepressants in J. Med. Chem., 1964, 7,625. Amino-substituted penthienoindoles with pharmacological properties are disclosed in U.S. Pat. No. 3,142, 678. 1,2,3,4-Tetrahydrocyclopent[b]indoles are disclosed in FR 2,242,983 and DE 2,438,413. 4-(3-Aminobutyl)-1,2,3,4-tetrahydrocyclopent[b]indole has been described in Khim. Geterotskikl. Soedin, 1970, 6, 371.

It is an object of this invention to provide selective, directly acting $5\text{-HT}_2$ receptor ligands for use in therapy and particularly for use as anti-obesity agents. It is a further object of this invention to provide directly acting ligands selective for $5\text{-HT}_{2B}$ and/or $5\text{-HT}_{2C}$ receptors, for use in therapy and particularly for use as anti-obesity agents. It is a further object of this invention to provide selective, directly acting $5\text{-HT}_{2C}$ receptor ligands, preferably $5\text{-HT}_{2C}$ receptor agonists, for use in therapy and particularly for use as anti-obesity agents.

It is a further object of this invention to provide compounds of formula (I) which are useful in the treatment and/or prevention of disorders involving elevated plasma blood glucose, particularly diabetes mellitus, Type II or non-insulin dependent diabetes mellitus (NIDDM); Type I or insulin dependent diabetes mellitus (IDDM); and Type III or malnutrition-related diabetes. The diabetes may be diabetes secondary to pancreatic disease; or diabetes related to steroid use.

SUMMARY OF THE INVENTION

The compounds of formula (I) are selective agonists of $5\text{-HT}_2$ receptors and are useful for the treatment of obesity and diabetes. The compounds of formula (I) are also useful in the treatment and/or prevention of the sequelae of hyperglycaemia; in the treatment and/or prevention of diabetic complications; and in the treatment of insulin dependence.

Compounds according to the invention are those of formula (I)

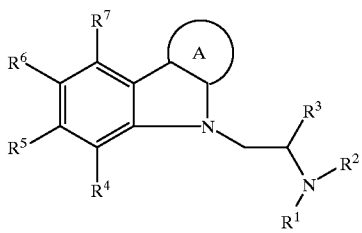

(I)

wherein
- $R^1$ and $R^2$ are independently selected from hydrogen, alkyl, alkenyl, alkinyl, and cycloalkyl;
- $R^3$ is alkyl, alkenyl, alkinyl, or cycloalkyl;
- $R^4$, $R^5$, $R^6$ and $R^7$ are independently selected from hydrogen, alkyl, alkenyl, alkinyl, cycloalkyl, halogen, haloalkyl, hydroxy, aryl, amino, mono- and dialkylamino, alkoxy, cycloalkyloxy, aryloxy, heteroaryloxy, alkylthio, alkylsulfoxyl, alkylsulfonyl, nitro, cyano, alkoxycarbonyl, aryloxycarbonyl, heteroaryloxycarbonyl, heteroaryl, alkylcarbonylamino, arylcarbonylamino, heteroarylcarbonylamino, and carboxyl;
- the ring A represents a 5 or 6 membered partially unsaturated or saturated carbocyclic or saturated or partially unsaturated heterocyclic ring, wherein the two atoms of the indoline ring to which ring A is fused form a saturated C—C single bond; and
- pharmaceutically acceptable salts, esters and/or addition compounds thereof.

DETAILED DESCRIPTION OF THE INVENTION

One aspect of the invention is directed to compounds of formula (I):

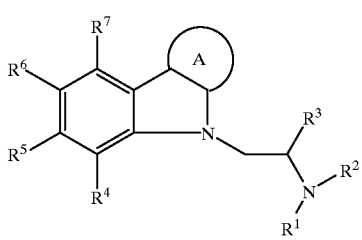

(I)

wherein
- $R^1$ and $R^2$ are independently selected from hydrogen, alkyl, alkenyl, alkinyl, and cycloalkyl;
- $R^3$ is alkyl, alkenyl, alkinyl, or cycloalkyl;
- $R^4$, $R^5$, $R^6$ and $R^7$ are independently selected from hydrogen, alkyl, alkenyl, alkinyl, cycloalkyl, halogen, haloalkyl, hydroxy, aryl, amino, mono- and dialkylamino, alkoxy, cycloalkyloxy, aryloxy, heteroaryloxy, alkylthio, alkylsulfoxyl, alkylsulfonyl, nitro, cyano, alkoxycarbonyl, aryloxycarbonyl, heteroaryloxycarbonyl, heteroaryl, alkylcarbonylamino, arylcarbonylamino, heteroarylcarbonylamino, and carboxyl;
- the ring A represents a 5 or 6 membered partially unsaturated or saturated carbocyclic or saturated or partially unsaturated heterocyclic ring, wherein the two atoms of the indoline ring to which ring A is fused form a saturated C—C single bond; and
- pharmaceutically acceptable salts, esters and/or addition compounds thereof.

In the present description the term "alkyl", alone or in combination, signifies a straight-chain or branched-chain alkyl group with 1 to 8 carbon atoms, preferably a straight or branched-chain alkyl group with 1–4 carbon atoms. Examples of straight-chain and branched $C_1$–$C_8$ alkyl groups are methyl, ethyl, propyl, isopropyl, butyl, isobutyl, tert.butyl, the isomeric pentyls, the isomeric hexyls, the isomeric heptyls and the isomeric octyls, preferably methyl, ethyl, propyl and isopropyl. Particularly preferred are methyl and ethyl.

The term "alkenyl" refers to a hydrocarbon chain as defined for alkyl having at least one olefinic double bond (including for example, vinyl, allyl and butenyl).

The term "alkinyl" refers to a hydrocarbon chain as defined for alkyl having at least one olefinic triple bond (including for example propinyl, butin-(1)-yl, etc).

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methylcyclohexyl, dimethylcyclohexyl, cycloheptyl and cyclooctyl, preferably cyclopropyl and particularly cyclopentyl.

The term "halogen" refers to fluoro, bromo, chloro and iodo.

The term "haloalkyl", alone or in combination, signifies an alkyl group as previously defined, wherein one or several hydrogen atoms, preferably one hydrogen atom have/has been replaced by halogen. Examples of haloalkyl groups are trifluoromethyl, pentafluoromethyl and trichloromethyl. Preferred examples are trifluoromethyl and difluoromethyl.

The term "hydroxy" refers to the group —OH, the term "cyano" to the group —CN.

The term "amino" refers to the group —$NH_2$.

The term "alkoxy", alone or in combination, means an alkyl ether group in which the term 'alkyl' has the significance given earlier, such as methoxy, ethoxy, n-propoxy, isopropoxy, n-butoxy, isobutoxy, sec.butoxy, tert.butoxy and the like.

The term "oxy", alone or in combination, refers to the group —O—.

The term "thio", alone or in combination, refers to the group —S—.

The term "sulfonyl" refers to the group —$S(O_2)$— and the term "sulfoxyl" to the group —S(O)—. "Hydroxy" means —OH, and "nitro" —$NO_2$.

The term "carboxyl" refers to the group —C(O)OH.

The term "carbonyl" refers to the group —C(O)— and the term "carbonylamino" refers to the group —C(O)—NH—.

The term "alkoxycarbonyl" refers to refers to a group of the formula —C(O)$R_C$ wherein $R_C$ is alkoxy as defined above.

The term "carbocyclic ring" refers to a ring wherein all the ring forming atoms are carbon atoms.

The term "aryl" for $R^4$, $R^5$, $R^6$ and $R^7$—alone or in combination—, refers to an aromatic carbocyclic radical, i.e. a 6 or 10 membered aromatic or partially aromatic ring, e.g. phenyl, naphthyl or tetrahydronaphthyl, preferably phenyl. The aryl moiety is optionally substituted with one or more, preferably one to three, groups independently selected from halogen, preferably fluoro, alkoxycarbonyl, e.g. methylcarbonyl, carboxy, cyano, alkyl, alkoxy, phenyl, phenoxy, trifluormethyl, trifluormethoxy, 1,3-dioxolyl, or 1,4-dioxolyl, alkylthio, alkylsulfoxyl and alkylsulfonyl. The most preferred groups are alkoxy and/or alkylsulfonyl.

The term "heteroaryl" for $R^4$, $R^5$, $R^6$ and $R^7$—alone or in combination—refers to an aromatic mono- or bicyclic radical having 5 to 10, preferably 5 to 6 ring atoms, containing one to three heteroatoms, preferably one heteroatom, e.g. independently selected from the group consisting of nitrogen, oxygen or sulfur. Examples of heteroaryl groups are pyridyl, pyrrolyl, quinolinyl, furanyl, thienyl, oxadiazolyl, thiadiazolyl, thiazolyl, oxazolyl, isoxazolyl, pyrazolyl, triazolyl, imidazolyl and pyrimidinyl. Preferred heteroarylgroups are thienyl, furanyl and pyridyl. The heteroaryl group is optionally substituted with one or more groups independently selected from halogen, preferably fluoro, alkoxycarbonyl, e.g. methylcarbonyl, carboxy, cyano, alkyl, alkoxy, phenyl, phenoxy, trifluormethyl, trifluormethoxy, 1,3-dioxolyl, or 1,4-dioxolyl, alkylthio, alkylsulfoxyl and alkylsulfonyl. The most preferred groups are alkoxy and/or alkylsulfonyl.

The term "heterocyclic ring"—alone or in combination—refers to a non-aromatic mono- or bicyclic radical having 5 to 10, preferably 5 to 6 ring atoms, containing one to three heteroatoms, preferably one heteroatom, e.g. independently selected from nitrogen, oxygen or sulfur. Optionally the heterocyclic ring can be substituted by a group independently selected from halogen, alkyl, alkoxy, oxocarboxy, alkoxycarbonyl, etc. and/or on a secondary nitrogen atom (i.e. —NH—) by alkyl, arylalkoxycarbonyl, alkylcarbonyl or on a tertiary nitrogen atom (i.e. =N—) by oxido. Examples for heterocyclic groups are morpholinyl, pyrrolidinyl, piperidyl, tetrahydrofuranyl and hexahydropyranyl, etc.

The term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids, particularly fumaric acid. Acceptable base salts include alkali metal (e.g. sodium, potassium), alkaline earth metal (e.g. calcium, magnesium) and aluminium salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "addition compounds" means any pharmaceutically acceptable addition compound of the compounds of formula (I). Addition compounds include those which are formed without change of valency from the union between a compound of formula (I) and one or more other molecules, particularly solvates, hydrates and inclusion complexes (such as cyclodextrin complexes).

The invention expressly includes pharmaceutically suitable derivatives of the compounds of formula I. In this context, the term "derivatives" means any pharmaceutically acceptable derivative of the compound of formula (I) which is metabolised in vivo to a compound of formula (I) (prodrug). For example, the COOH groups in $R^4$ to $R^7$ can be esterified. The alkyl and aralkyl esters are examples of suitable esters. The methyl, ethyl, propyl, butyl and benzyl esters are preferred esters. The methyl and ethyl esters are especially preferred.

The compounds of formula I can also be solvated, e.g. hydrated. The solvation can be effected in the course of the manufacturing process or can take place e.g. as a consequence of hygroscopic properties of an initially anhydrous compound of formula I (hydration).

The compounds of formula I can contain several asymmetric centres and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluent).

It is preferred that the compounds of formula (I) are selected from those wherein $R^1$ and $R^2$ are independently selected from hydrogen or alkyl. In one embodiment, the compounds of formula (I) are selected from compounds in which $R^1$ is the same as $R^2$. Preferably $R^1$ and $R^2$ are hydrogen.

The compounds of formula (I) are preferably selected from compounds in which $R^3$ is alkyl or cycloalkyl, preferably alkyl, and more preferably methyl.

Preferably, $R^4$, $R^6$ and $R^7$ are independently selected from hydrogen, halogen, alkyl and alkoxy. More preferably, $R^4$ is hydrogen. $R^6$ is preferably hydrogen, halogen or alkoxy, more preferably hydrogen or fluoro. $R^7$ preferably is hydrogen, halogen or alkoxy, more preferably hydrogen, chloro or methoxy.

In another preferred embodiment, $R^5$ is hydrogen, halogen, alkoxy, or heteroarylcarbonylamino, preferably hydrogen, chloro, methoxy, pyridylcarbonylamino or thienylcarbonylamino.

As mentioned above, the ring A represents a 5 or 6 membered a partially unsaturated or saturated carbocyclic or heterocyclic ring, wherein the two atoms of the indoline ring to which ring A is fused form a saturated C—C single bond. In a preferred embodiment of the invention, the ring A is a 5-membered ring, e.g. a saturated or partially unsaturated ring, e.g. cyclopentyl, cyclopentenyl, tetrahydrofuranyl and dihydrofuranyl, preferably a saturated carbocyclic ring, e.g. cyclopentyl.

In another preferred embodiment of the present invention, ring A may be selected from the group consisting of morpholinyl, piperidinyl, tetrahydropyranyl, dihydropyranyl, tetrahydrofuranyl and dihydrofuranyl, optionally substituted with alkyl or oxo.

The ring A may be substituted or unsubstituted. Where substituted, there will generally be 1 to 3 substituents present, preferably 1 substituent. Substituents may include:

a) carbon-containing groups as alkyl, alkenyl, alkinyl, aryl (e.g. substituted and unsubstituted phenyl, arylalkyl (e.g. substituted and unsubstituted benzyl);

b) halogen atoms and halogen containing groups such as haloalkyl (e.g. trifluoromethyl), haloaryl (e.g. chlorophenyl);

c) oxygen containing groups such as oxo, alcohols (e.g. hydroxy, hydroxyalkyl, hydroxyaryl, (aryl)(hydroxy)alkyl), ethers (e.g. alkoxy, aryloxy, alkoxyalkyl, aryloxyalkyl, alkoxyaryl, aryloxyaryl), aldehydes (e.g. carboxaldehyde), ketones (e.g. alkylcarbonyl, arylcarbonyl, alkylcarbonylalkyl, alkylcarbonylaryl, arylcarbonylalkyl, arylcarbonylaryl, arylalkylcarbonyl, arylalkylcarbonylalkyl, arylalkylcarbonylaryl);

d) acids (e.g. carboxy, carboxyalkyl, carboxyaryl), acid derivatives such as esters (e.g. alkoxycarbonyl, aryloxycarbonyl, alkoxycarbonylalkyl, aryloxycarbonylalkyl, alkoxycarbonylaryl, aryloxycarbonylaryl, alkylcarbonyloxy, alkylcarbonyloxyalkyl);

e) amides (e.g. aminocarbonyl, mono- or dialkylaminocarbonyl, aminocarbonylalkyl, mono- or dialkylaminocarbonylalkyl, arylaminocarbonyl or arylalkylaminocarbonyl, alkylcarbonylamino, arylcarbonylamino or arylalkylcarbonylamino), f) carbamates (e.g. alkoxycarbonylamino, aryloxycarbonylamino, arylalkyloxycarbonylamino, aminocarbonyloxy, mono- or dialkylaminocarbonyloxy, arylaminocarbonyloxy or arylalkylaminocarbonyloxy);

g) ureas (e.g. mono- or di-alkylaminocarbonylamino, arylaminocarbonylamino or arylalkylaminocarbonylamino);

h) nitrogen containing groups such as amines (e.g. amino, mono- or dialkylamino, arylamino, aminoalkyl, mono- or dialkylaminoalkyl), azides, nitriles (e.g. cyano, cyanoalkyl), nitro;

i) sulfur containing groups such as thiols, thioethers, sulfoxides, and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl; and j) heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The preferred substituents may be selected from hydrogen or alkyl.

Especially preferred compounds of the present invention are (2'S, 3aS, 8bS)-1-[4-(6-chloro-1,2,3,3a,4,8b-hexahydrocyclopent[b]indolyl]-2-propylamine, (2'S)-1-[4-(7-fluoro-6-1,2,3,3a,4,8b-hexahydro-6-methoxycycyclopent[b]indolyl)]-2-propylamine, and (2'S)-1-[4-(7-fluoro-1,2,3,3a,4,8b-hexahydrocyclo-8-methoxypent[b]indolyl)]-2-propylamine.

The invention also refers to pharmaceutical compositions containing a compound as defined above and a pharmaceutically acceptable excipient. The invention also refers to a process for the preparation of a pharmaceutical composition comprising combining a compound of formula (I) as set out above with a pharmaceutically acceptable carrier or excipient. The invention refers also to a compound of formula (I) as set out above for use in therapy.

Further, the invention refers to the use of a compound of formula (I) as set out above in the manufacture of a medicament for the treatment of disorders of the central nervous system; damage to the central nervous system; cardiovascular disorders; gastrointestinal disorders; diabetes insipidus, and sleep apnea. In the above use the disorders of the central nervous system are selected from depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, obesity, bulimia, anorexia nervosa and premenstrual tension. In a preferred embodiment of the invention the damage to the central nervous system as mentioned above is by trauma, stroke, neurodegenerative diseases or toxic or infective CNS diseases. In the above use toxic or infective CNS disease is encephalitis or meningitis and the cardiovascular disorder is thrombosis. In the above use the gastrointestinal disorder is dysfunction of gastrointestinal motility. An especially preferred embodiment of the present invention is the above use wherein said medicament is for the treatment of obesity. A further preferred embodiment of the present invention is the use of a compound of formula (I) in the manufacture of a medicament for the treatment of diabetes mellitus, Type I diabetes, Type II diabetes, diabetes secondary to pancreatic disease, diabetes related to steroid use, Type III diabetes, hyperglycaemia, diabetic complications and insulin resistance. Particularly preferred is the above use of a compound of formula (I) for the treatment of Type II diabetes. The treatment in the above uses may be a prophylactic treatment. The invention also relates to the use of compounds as 5-$HT_{2C}$ receptor agonists.

The invention also relates to a method of treatment of any of the disorders set out in above comprising administering to a patient in need of such treatment an effective dose of a compound of formula (I) as set out above. The method of treatment of any of the disorders set out above may be prophylactic treatment. In a preferred embodiment the disorder in the above method of treatment may be obesity. In a further preferred embodiment the disorders in the above method of treatment are selected from diabetes mellitus, Type I diabetes, Type II diabetes, diabetes secondary to pancreatic disease, diabetes related to steroid use, Type III diabetes, hyperglycaemia, diabetic complications and insulin resistance. Particularly preferred is the above method of treatment wherein said disorder is Type II diabetes. The above methods of treatments may be prophylactic treatments.

The invention also comprises a process for the preparation of a compound of formula (I) as defined above comprising a) reaction of a compound of formula (IV)

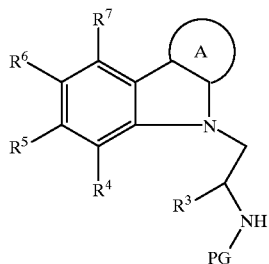

(IV)

wherein A, $R^3$ to $R^7$ are as above and PG is an NH-protecting group, e.g. tert-butoxycarbonyl, benzyloxycarbonyl, ethoxycarbonyl and 9-fluorenylmethoxycarbonyl, with a reagent suitable to remove the protecting group for the preparation of compounds of formula (I) in which $R^1$ and $R^2$ are hydrogen, e.g. tert-butoxycarbonyl can be removed using an acid e.g. hydrochloric acid, trifluoroacetic acid or methanesulfonic acid, benzyloxycarbonyl can be removed using catalytic hydrogenolysis over a catalyst such as palladium on carbon or palladium hydroxide or by hydrolysis in the presence of a base such as sodium hydroxide or by treatment with hydrogen bromide in acetic acid or by treatment with a Lewis Acid such as boron tribromide or trimethylsilyliodide, ethoxycarbonyl can be removed by hydrolysis in the presence of a base such as sodium hydroxide or by treatment with hydrogen bromide in acetic acid or by treatment with a Lewis Acid such as boron tribromide or trimethylsilyliodide and 9-fluorenylmethoxycarbonyl can be removed by treatment with a base such as morpholine or sodium hydroxide, or b) for the preparation of compounds of formula (I) in which $R^1$ and $R^2$ are as defined above without being hydrogen or only one of $R^1$ and $R^2$ is hydrogen by reductive alkylation of a compound prepared according to step a).

Further, the invention relates to a compound prepared by a process as defined above.

Compounds of the invention can be conveniently prepared according to the Reaction Scheme (below; $R^1$ to $R^7$ and A are as defined above and PG is a protecting group, e.g. tert-butoxycarbonyl, benzyloxycarbonyl and ethoxycarbonyl). Reaction of indole (II) with an alkylating agent such as tert-butyl [2-[(1-methanesulfonyl)oxy]propyl] carbamate in the presence of a base such as potassium hydroxide in a solvent such as methyl sulfoxide gives indole-carbamate (III). Reduction of (III) with a reducing agent e.g. sodium cyanoborohydride in a solvent such as acetic acid produces indoline-carbamate (IV). The individual diastereoisomers of (IV) may then be separated using, for example, column chromatography, HPLC, or recrystallisation. A compound of formula (I) where $R_1=R_2=H$ can be prepared by treatment of (IV) with an acid such as hydrochloric acid in a suitable solvent such as methanol. A compound of formula (I) where $R_1$ and/or $R_2$=alkyl can be prepared from a compound of formula (I) where $R_{1=R2}=H$ by reductive alkylation using an aldehyde or ketone in the presence of a reducing agent such as formic acid, sodium cyanoborohydride or sodium triacetoxyborohydride.

Reaction Scheme

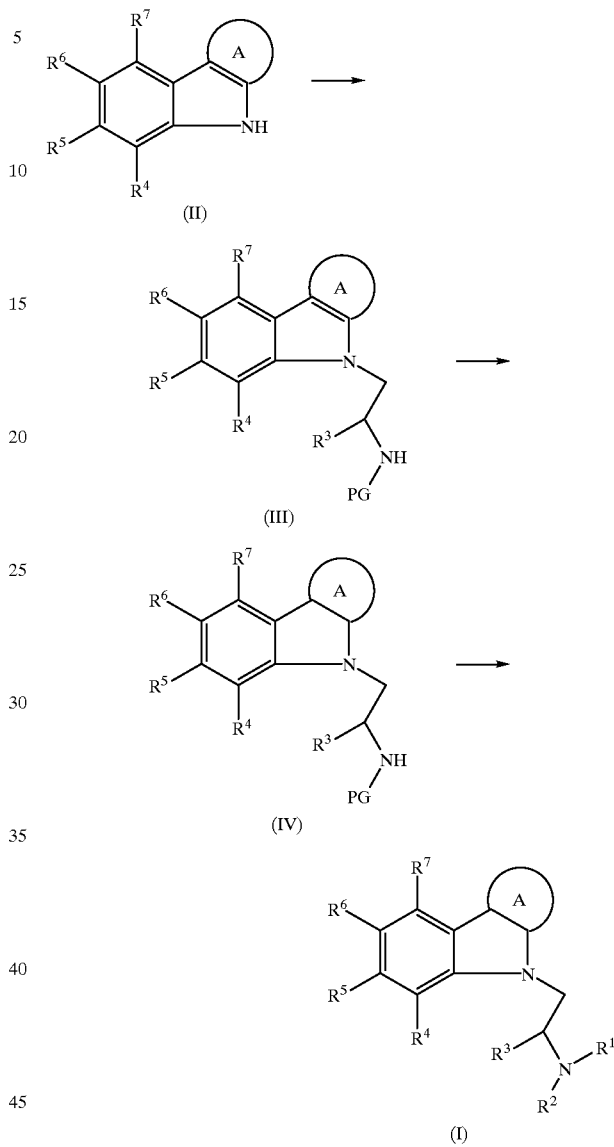

Indoles of formula (II) may be obtained by treatment of a phenylhydrazine with a ketone under acidic conditions in a suitable solvent, such as ethanol or water with heating where necessary. Where appropriate the phenylhydrazine may be synthesised from the corresponding aniline according to methods known to those skilled in the art e.g. sequential reaction with sodium nitrite and tin(II)chloride in a solvent such as water in the presence of an acid such as hydrochloric acid.

If, in any of the other processes mentioned herein, the substituent group $R^4$, $R^5$, $R^6$ or $R^7$ is other than the one required, the substituent group may be converted to the desired substituent by known methods. The substituents $R^4$, $R^5$, $R^6$ or $R^7$ may also need protecting against the conditions under which the reaction is carried out. In such a case, the protecting group may be removed after the reaction has been completed.

Assay Procedures

1. Binding to Serotonin Receptors

The binding of compounds of formula (I) to serotonin receptors was determined in vitro by standard methods. The preparations were investigated in accordance with the assays given hereinafter.

Method (a): For the binding to the 5-$HT_{2C}$ receptor the 5-$HT_{2C}$ receptors were radiolabelled with [$^3$H]-5-HT. The affinity of the compounds for 5-$HT_{2C}$ receptors in a CHO cell line was determined according to the procedure of D. Hoyer, G. Engel and H. O. Kalkman, *European J. Pharmacol.*, 1985, 118, 13–23.

Method (b): For the binding to the 5-$HT_{2B}$ receptor the 5-$HT_{2B}$ receptors were radiolabelled with [$^3$H]-5-HT. The affinity of the compounds for human 5-$HT_{2B}$ receptors in a CHO cell line was determined according to the procedure of K. Schmuck, C. Ullmer, P. Engels and H. Lubbert, *FEBS Lett.*, 1994, 342, 85–90.

Method (c): For the binding to the 5-$HT_{2A}$ receptor the 5-$HT_{2A}$ receptors were radiolabelled with [$^{125}$I]-DOI. The affinity of the compounds for 5-$HT_{2A}$ receptors in a CHO cell line was determined according to the procedure of D. J. McKenna and S. J. Peroutka, *J. Neurosci.*, 1989, 9/10, 3482–90.

The thus determined activities of the Examples are shown in Table 1.

TABLE 1

Radioligand Binding Data

| Compound | $K_i$ (2C) | $K_i$ (2B) | $K_i$ (2A) |
|---|---|---|---|
| Example 2 | 133 nM | 302 nM | 726 nM |
| Example 10 | 164 nM | 109 nM | 983 nM |
| Example 19 | 88 nM | 513 nM | 1156 nM |
| Example 20 | 318 nM | 367 nM | 481 nM |

Functional Activity

The functional activity of compounds of formula (I) was assayed using a Fluorimetric Imaging Plate reader (FLIPR):

CHO cells expressing either the h5-$HT_{2C}$ or h5-$HT_{2A}$ receptors were counted and plated into standard 96 well microtitre plates before the day of testing to give a confluent monolayer. The following day the cells were dye-loaded with the calcium sensitive dye Fluo 3-AM by incubation with serum free culture maintenance media containing pluronic acid and Fluo 3-AM dissolved in DMSO at 37° C. in a $CO_2$ incubator at 95% humidity for approximately 90 minutes. Unincorporated dye was removed by washing with Hanks balanced salt solution containing 20 mM HEPES and 2.5 mM probenecid (the assay buffer) using an automated cell washer to leave a total volume of 100 μl/well.

The drug (dissolved in 50 μL of assay buffer) was added at a rate of 70 μL/sec to each well of the FLIPR 96 well plate during fluorescence measurements. The measurements are taken at 1 sec intervals and the maximum fluorescent signal was measured (approx 10–15 secs after drug addition) and compared with the response produced by 10 μM 5-HT (defined as 100%) to which it is expressed as a percentage response (relative efficacy). Dose response curves were constructed using Graphpad Prism (Graph Software Inc.).

The thus determined activities of the Examples are shown in Table 2.

TABLE 2

Functional Data

| Compound | h5-$HT_{2A}$ | | h5-$HT_{2C}$ | |
|---|---|---|---|---|
| | $EC_{50}$ (nM) | Relative Efficacy (%) | $EC_{50}$ (nM) | Relative Efficacy (%) |
| Example 2 | 10000 | 7 | 585 | 90 |
| Example 10 | 10000 | 20 | 737 | 84 |
| Example 19 | 10000 | 0 | 391 | 84 |
| Example 20 | 5490 | 17 | 464 | 62 |

According to a further aspect of the invention there is provided a method of treatment of obesity in a human in need of such treatment which comprises administration to the human a therapeutically effective amount of a compound according to formula I and a therapeutically effective amount of a lipase inhibitor, particularly preferred, wherein the lipase inhibitor is orlistat. According to a further aspect of the invention there is provided a method of treatment of diabetes mellitus, Type I diabetes, Type II diabetes, diabetes secondary to pancreatic disease, diabetes related to steroid use, Type III diabetes, hyperglycaemia, diabetic complications and insulin resistance in a human in need of such treatment which comprises administration to the human a therapeutically effective amount of a compound according to formula I and a therapeutically effective amount of a lipase inhibitor, particularly preferred, wherein the lipase inhibitor is orlistat. Particularly preferred is the above method for the treatment of Type II diabetes in a human in need of such treatment which comprises administration to the human a therapeutically effective amount of a compound according to formula I and a therapeutically effective amount of a lipase inhibitor, particularly preferred, wherein the lipase inhibitor is orlistat. Also subject of the present invention is the mentioned method, wherein the administration is simultaneous, separate or sequential. The mentioned treatment in the above method of treatment may be a prophylactic treatment.

A further preferred embodiment of the present invention is the use of a compound of the formula I in the manufacture of a medicament for the treatment and prevention of obesity in a patient who is also receiving treatment with a lipase inhibitor, particularly preferred, wherein the lipase inhibitor is orlistat. Another preferred embodiment of the present invention is the use of a compound according to formula (I) in the manufacture of a medicament for the treatment and prevention of diabetes mellitus, Type I diabetes, Type II diabetes, diabetes secondary to pancreatic disease, diabetes related to steroid use, Type III diabetes, hyperglycaemia, diabetic complications and insulin resistance in a patient who is also receiving treatment with a lipase inhibitor, particularly preferred, wherein the lipase inhibitor is orlistat. Further particularly preferred is the above use of a compound according to formula (I) for the treatment and prevention of Type II diabetes in a patient who is also receiving treatment with a lipase inhibitor, particularly preferred, wherein the lipase inhibitor is orlistat. The treatment in the above uses may be a prophylactic treatment.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495. Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater. Orlistat can be administered to humans in conventional oral compositions, such as, tablets, coated tablets, hard and soft gelatin capsules, emulsions or suspensions. Examples of carriers which can be used for tablets, coated tablets, dragées and hard gelatin capsules are lactose, other sugars and sugar alcohols like sorbitol, mannitol, maltodextrin, or other fillers; surfactants like sodium lauryle sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004, 996, respectively.

As mentioned earlier, medicaments containing a compound of formula I are also an object of the present invention as is a process for the manufacture of such medicaments, which process comprises bringing one or more compounds of formula I and, if desired, one or more other therapeutically valuable substances into a galenical administration form.

The pharmaceutical compositions may be administered orally, for example in the form of tablets, coated tablets, dragées, hard or soft gelatin capsules, solutions, emulsions or suspensions. Administration can also be carried out rectally, for example using suppositories; locally or percutaneously, for example using ointments, creams, gels or solutions; or parenterally, for example using injectable solutions.

For the preparation of tablets, coated tablets, dragees or hard gelatin capsules the compounds of the present invention may be admixed with pharmaceutically inert, inorganic or organic excipients. Examples of suitable excipients for tablets, dragées or hard gelatin capsules include lactose, maize starch or derivatives thereof, talc or stearic acid or salts thereof.

Suitable excipients for use with soft gelatin capsules include for example vegetable oils, waxes, fats, semi-solid or liquid polyols etc.; according to the nature of the active ingredients it may however be the case that no excipient is needed at all for soft gelatin capsules.

For the preparation of solutions and syrups, excipients which may be used include for example water, polyols, saccharose, invert sugar and glucose.

For injectable solutions, excipients which may be used include for example water, alcohols, polyols, glycerine, and vegetable oils.

For suppositories, and local or percutaneous application, excipients which may be used include for example natural or hardened oils, waxes, fats and semi-solid or liquid polyols.

The pharmaceutical compositions may also contain preserving agents, antioxidants, solubilising agents, stabilizing agents, wetting agents, emulsifiers, sweeteners, colorants, odorants, salts for the variation of osmotic pressure, buffers, coating agents or antioxidants. They may also contain other therapeutically valuable agents.

The dosages in which the compounds of formula I are administered in effective amounts depend on the nature of the specific active ingredient, the age and the requirements of the patient and the mode of application. In general, dosages of 0.1–100 mg/kg body weight per day come into consideration, although the upper limit quoted can be exceeded when this is shown to be indicated.

The following specific examples are provided as a guide to assist in the practice of the invention, and are not intended as a limitation on the scope of the invention.

EXAMPLES

Example I (3aR,8bR) and (3aS,8bS)2-(1,2,3,3a,4,8b-Hexahydrocyclopent[b]indol-4-yl)-ethylamine Fumarate A) 2-(1,2,3,4-Tetrahydrocyclopent[b]indol-4-yl)-ethylamine Hydrochloride A mixture of 1,2,3,4-tetrahydrocyclopent[b]indole (2.0 g, 13 mmol), powdered sodium hydroxide (2.0 g, 50 mmol) and tetrabutylammonium hydrogensulfate (0.17 g, 0.5 mmol) in acetonitrile (60 mL) was stirred for 10 min. To the mixture was added chloroethylamine hydrochloride (2.2 g, 19 mmol) and the mixture was heated to reflux, stirred for 90 min then cooled to room temperature. The mixture was poured into water (100 mL) and extracted twice with ether (100 mL). The combined organic extracts were washed (water, brine), dried (sodium sulfate) and concentrated in vacuo to give a yellow oil (2.65 g). The oil was dissolved in ether (50 mL) and added dropwise to a stirred solution of ethereal hydrogen chloride (1.0 M, 13 mL, 13 mmol) in added ether (35 mL). The mixture was cooled to 0° C., stirred for 15 min then filtered. The filter-cake was washed with ether and dried in vacuo to give the product as an off-white solid (2.66 g, 88%); m.p. 276–277° C.; Found: C, 65.37; H, 7.22; N, 11.66%. $C_{13}H_{17}N_2Cl.0.125H_2O$ requires: C, 65.33; H, 7.28; N, 11.72%.

B) tert.Butyl-2-[4-(1,2,3,4-tetrahydrocyclopent[b]indolyl)]ethylcarbamate

To a stirred solution of 2-(1,2,3,4-tetrahydrocyclopent[b]indol-4-yl)ethylamine hydrochloride (1.0 g, 4.2 mmol) in 2-propanol (15 mL) and water (15 mL) was added dropwise a solution of sodium hydroxide (0.34 g, 8.5 mmol) in water (5 mL). The mixture was stirred for 5 min then di-tert-butyl dicarbonate (1.0 g, 4.6 mmol) was added and the mixture was stirred for a further 1 h. The precipitate was filtered-off, washed with water and dried in vacuo to give the crude product as a white solid (1.32 g, >100%) which was used without further purification; NMR (400 MHz, $CDCl_3$) $\delta_H$7.42 (1H, dd, J 1.5, 7 Hz), 7.25 (1H, d, J 7 Hz), 7.08 (2H, m), 4.53 (1H, m, NH), 4.16 (2H, t, J 6 Hz), 3.44 (2H, q, J 6 Hz), 2.84 (4H, t, J 7 Hz), 2.53 (2H, quint, J 7 Hz) and 1.43 (9H, s); HPLC: [Xterra; 2.0 ml/min, gradient elution, methanol-10 mM aqueous ammonium acetate solution (50:50) to (80:20) over 4 min then (80:20)] 97% (6.72 min).

C) tert.Butyl-2-[4-(1,2,3,3a,4,8b-hexahydrocyclopent[b]indolyl)]ethylcarbamate

To a stirred solution of tert.Butyl-2-[4-(1,2,3,4-tetrahydrocyclopent[b]indolyl)]ethylcarbamate (0.20 g, 0.66 mmol) in acetic acid (5 mL) was added sodium cyanoborohydride (0.13 g, 2.0 mmol). The mixture was stirred for 2 h then poured into aqueous sodium hydroxide solution (2 N, 30 mL) and extracted with two portions of ether (20 mL). The combined organic extracts were washed (water, brine), dried (sodium sulfate) and concentrated in vacuo to give the crude product as a viscous oil (0.216 g, >100%) which was used without further purification. NMR (400 MHz, $CDCl_3$) $\delta_H$6.99 (2H, dt, J 1.5, 7 Hz), 6.64 (1H, dt, J 1, 7 Hz), 6.34 (1H, d, J 7 Hz), 4.77 (1H, m, NH), 4.13 (1H, m), 3.72 (1H, dt, J 3, 9 Hz), 3.30 (2H, m), 3.26 (2H, m), 1.99 (1H, m), 1.79 (2H, m), 1.62 (2H, m), 1.51 (1H, m) and 1.42 (9H, s); HPLC: [Xterra; 2.0 ml/min, gradient elution, methanol-10 mM aqueous ammonium acetate solution (50:50) to (80:20) over 4 min then (80:20)] 95% (6.64 min).

D) (3aR, 8bR) and (3aS, 8bS)2-(1,2,3,3a,4,8b-Hexahydrocyclopent[b]indol-4-yl)-ethylamine Fumarate A stirred solution of tert.Butyl-2-[4-(1,2,3,3a,4,8b-hexahydrocyclopent[b]indolyl)]ethylcarbamate (0.15 g, 0.5 mmol) and concentrated hydrochloric acid (0.2 mL) in methanol (5 mL) was heated to reflux, stirred for 4 h, cooled to room temperature and poured into water (30 mL). The mixture was washed with ether (10 mL); the ether wash was discarded. The aqueous layer was basified with aqueous sodium hydroxide solution (2 N, 5 mL) then extracted with ether (2×20 mL). The combined ether extracts were washed (water, brine), dried (sodium sulfate) and concentrated in vacuo to give a yellow oil (0.067 g). The oil was dissolved in hot 2-propanol (1 mL) and added dropwise to a stirred solution of fumaric acid (0.06 g) in hot 2-propanol (1 mL). The solution was cooled to 0° C., diluted with ether (5 mL) and filtered. The filter-cake was washed (ether) and dried in vacuo to give the product as a white solid (0.081 g, 51%); m.p. 172° C. (dec.); NMR (400 MHz, DMSO-$d_6$) $\delta_H$6.96 (2H, t, J 7.5 Hz), 6.53 (1H, t, J 7.5 Hz), 6.46 (2H, s), 6.41 (1H, d, J 7.5 Hz), 4.18 (1H, m), 3.69 (1H, dt, J 3, 9 Hz), 3.34 (2H, m), 2.92 (2H, m), 1.97 (1H, m), 1.74 (1H, m), 1.62 (2H, m) and 1.40 (1H, m).

Example II

Preparation of Starting Compounds

Compounds of formula A

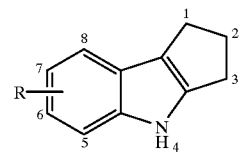

wherein R represents the substitution pattern consisting of $R^4$, $R^5$, $R^6$ and $R^7$ as defined in formula (I) may be prepared according to the Fischer indole synthesis (see for example Catal. Lett., 1999, 61(1,2), 93–97). Phenylhydrazines may be used as starting compounds. Phenylhydrazines are commercially available or may be prepared as shown below for 4-fluoro-3-methoxyphenylhydrazine hydrochloride.

A) Preparation of Phenylhydrazines: 4-Fluoro-3-methoxyphenylhydrazine Hydrochloride To stirred hydrochloric acid (100 mL) at 0° C. was added 3-methoxy-4-fluoroaniline (10 g, 71 mmol) followed by water (10 mL) and more hydrochloric acid (10 mL). The mixture was warmed to room temperature, stirred for 20 min then cooled to −5° C. A solution of sodium nitrite (5.14 g, 75 mmol) in water (25 mL) was added dropwise such that the internal temperature remained below 0° C. The mixture was warmed to room temperature and stirred for 2 h. The mixture was cooled to −5° C. and a solution of tin(II) chloride dihydrate (64 g, 284 mmol) in hydrochloric acid (200 mL) was added dropwise such that the internal temperature remained below 0° C. The mixture was warmed to room temperature, stirred for 3 h then filtered. The filter-cake was washed with hydrochloric acid and dried in vacuo to give a pink solid (7.4 g). The emerging precipitate from the combined filtrates was filtered-off, washing with hydrochloric acid, to give a further crop of product (1.8 g. Combined yield 9.2 g, 67%); m.p. 250+° C. (dec.); NMR: (400 MHz, DMSO-$d_6$) $\delta_H$10.17 (3H, s, $NH_3$), 8.14 (1H, s, NH), 7.15 (1H, dd,J 11.6, 8.6 Hz), 6.95 (1H, dd, J 7.6, 3.0 Hz), 6.54 (1H, dt, J 8.6, 3.0 Hz), 3.83 (3H, s, MeO).

B-1) Synthesis of Ring A: 1,2,3,4-Tetrahydrocyclopent[b]indole (Examples 1a and 4a–7a)

A solution of phenylhydrazine (32.44 g, 300 mmol) in 2-propanol (300 mL) was treated with cyclopentanone (27 mL, 25.7 g, 305 mmol). The solution was stirred at 20° C. for 1 h and poured onto mixture of ice (900 g) and water (300 mL). The chilled mixture was stirred until the ice had melted then filtered. The filter-cake was washed with water (2×300 mL) an the resultant damp solid (85 g) was added to water (540 mL). The stirred suspension was treated with concentrated sulfuric acid (33 mL, 61 g, 600 mmol) then heated under reflux for 30 min, cooled to 0° C. and stirred for 15 min. The dark red solid was filtered off, washed with water (2×60 mL) and air-dried for 18 h. The crude product was added to dichloromethane (300 mL), stirred for 30 min then filtered, washing with dichloromethane (100 mL). The filtrate was treated with silica (48 g), stirred for 1 h, filtered and washed with dichloromethane (400 mL). The filtrate was concentrated to give a solid, which was triturated with hexane to give 1,2,3,4-tetrahydrocyclopent[b]indole (30 g, 65%) as a pink solid. Analytical data for 1,2,3,4-tetrahydrocyclopent[b]indole are included in Table 3 below.

Where the intermediate hydrazone was obtained as an oil the following method was used:

A solution of the arylhydrazine (100 mmol) in benzene (100 mL) was treated with cyclopentanone (9 mL, 8.6 g, 102 mmol). The solution was heated under reflux with azeotropic removal of water for 30–60 min. The solution was allowed to cool and was concentrated in vacuo to give the arylhydrazone as an oil which was used directly in the cyclisation step as described above.

B-2) Synthesis of Ring A: 1,2,3,4-Tetrahydro-6-methoxycyclopent[b]indole (Examples 21a and 22a)

To stirred, degassed ethanol (20 mL), shielded from light and under an atmosphere of Ar at ambient temperature, was added 3-methoxyphenylhydrazine hydrochloride (1.0 g, 5.6 mmol) and cyclopentanone (0.5 mL, 5.7 mmol). The mixture was heated under reflux for 24 h, cooled to room temperature then poured onto 300 mL ice-water and made basic with saturated aqueous sodium bicarbonate solution (to pH 8). The suspension was filtered, and the resultant solid was washed with water and dried to afford the crude product as a dark brown solid (0.95 g, 89%). Purification by flash column chromatography [SiO$_2$; iso-hexane-dichloromethane (3:2→1:1)] afforded the separated isomeric indole products.

Alternatively, purification of the crude product was achieved by dissolution in dichloromethane, then filtration through a plug of silica and concentration in vacuo followed by trituration with toluene, filtration, and washing of the resultant solid with ice-cold toluene-heptane (1:1) to afford exclusively the 6-isomer. Data for 1,2,3,4-tetrahydro-6-methoxycyclopent[b]indole are listed in Table 3 below.

For the appropriate examples, pentindole regioisomers arising from the use of unsymmetrical arylhydrazines were separated by recrystallisation from toluene, cyclohexane, isohexane or ethanol or by trituration with toluene or pentane.

TABLE 3

Starting compounds

A

| Example (method) | Starting Compound: phenylhydrazines | Compound of formula A | R | Data |
|---|---|---|---|---|
| 2a, 3a (i) | 3-chloro-phenylhydrazine | 6-Chloro-1,2,3,4-tetrahydrocyclopent[b]-indole | 6-Cl | m.p. 188–191° C. (EtOH); Found: C, 69.21; H, 5.18; N, 7.31% C$_{11}$H$_{10}$ClN requires C, 68.94; H, 5.26; N, 7.30%. |
| 4a–7a (i) | phenylhydrazine | 1,2,3,4-Tetrahydrocyclopent[b]-indole | H | m.p. 107–108° C. (hexane); Found: C, 83.04; H, 7.12; N, 8.78%. C$_{11}$H$_{11}$N.0.1H$_2$O requires C, 83.09; H, 7.10; N, 8.81%. |
| 8a, 9a, 18a, 19a (ii) | 4-fluoro-3-methoxyphenyl-hydrazine | 7-Fluoro-6-methoxy-1,2,3,4-tetrahydrocyclopent[b]-indole | 7-F, 6-OMe | Crude product stirred in toluene for 10 min, filtered and the filter-cake dried under vacuum. Used without further purification; NMR (400 MHz, DMSO-d$_6$) δ$_H$ 10.69(1H, s, NH), 7.08(1H, d, J 12.0Hz), 6.98(1H, d, J 7.6Hz), 3.83(3H, s, MeO), 2.79(2H, m), 2.69(2H, t, J 7.0Hz), 2.50(2H, m). |
| 10a, 11a, 16a, 17a (i) | 3-chloro-4-fluorophenyl-hydrazine | 6-Chloro-7-fluoro-1,2,3,4-tetrahydrocyclopent[b]-indole | 6-Cl, 7-F | m.p. 139.5–140° C. (cyclohexane); Found: C, 62.87; H, 4.35; N, 6.69%. C$_{11}$H$_9$ClFN requires C, 63.02; H, 4.33; N, 6.68%. |
| 12a, 13a (i) | 3-chloro-4-methylphenyl-hydrazine | 8-Chloro-7-methyl-1,2,3,4-tetrahydrocyclopent[b]-indole | 8-Cl, 7-Me | Low-melting solid; NMR (400 MHz, CDCl$_3$) δ$_H$ 7.61(1H, m, NH), 6.97(1H, d, J 8Hz), 6.87(1H, d, J 8Hz), 3.01(2H, tt, J 1.5, 7Hz), 2.75(2H, tt, J 1.5, 7Hz), 2.47 (2H, m) and 2.41(3H, s). HPLC: [Supelcosil ABZ+; 1.0 ml/min, methanol-10 mM aqueous ammonium acetate solution (80:20)] 90% (8.90 min) [and 6-chloro-7-methyl 10% (8.54 min)]. |
| 14a, 15a (i) | 3-chloro-4-fluorophenyl-hydrazine | 8-Chloro-7-fluoro-1,2,3,4-tetrahydrocyclopent[b]-indole | 8-Cl, 7-F | Low-melting solid. NMR (400 MHz, CDCl$_3$) δ$_H$ 7.86(1H, m, NH), 7.07(1H, dd, J 3.5, 9Hz), 6.86(1H, t, J 9Hz), 3.03(2H, tt, J 1.5, 7Hz), 2.84(2H, t, J 7Hz) and 2.53 (2H, quintet, J 7Hz); HPLC: [Xterra; 2.0 ml/min, methanol - 10 Mm aqueous ammonium acetate solution (80:20)] 99.5% (8.29 min). |
| 20a (ii) | 4-fluoro-3-methoxy-phenylhydrazine | 7-Fluoro-8-methoxy-1,2,3,4-tetrahydrocyclopent[b]-indole | 7-F, 8-OMe | From column chromatography of the mother liquors from Examples 8a, 9a, 18a and 19a. Used immediately without further purification or analysis. |

TABLE 3-continued

Starting compounds

A

| Example (method) | Starting Compound: phenylhydrazines | Compound of formula A | R | Data |
|---|---|---|---|---|
| 21a, 22a (ii) | 3-methoxyphenyl-hydrazine | 6-methoxy-1,2,3,4-tetrahydrocyclopent[b]-indole | 6-OMe | m.p. 136–137.5° C.; NMR (400 MHz, CDCl$_3$) $\delta_H$ 7.68(1H, m, NH), 7.29(1H, d, J 8.5Hz), 6.81(1H, d, J 2Hz), 6.74(1H, dd, J 2, 8.5Hz), 3.83(3H, s), 2.85–2.76(4H, m), 2.55–2.47(2H, m). |

Example III

Indole Alkylation

Compounds of formula B

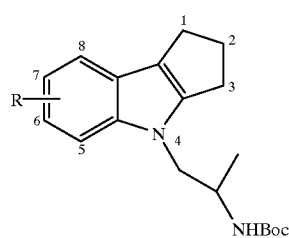

wherein R represents the substitution pattern consisting of R$^4$, R$^5$, R$^6$ and R$^7$ as defined in formula (I) are available via indole alkylation according to the following example:
Preparation of (R)-tert-butyl-[2-[1-[4-(1,2,3,4-tetrahydrocyclopent[b]indolyl)]]pro-pyl]carbamate (Examples 4b and 5b)

Methyl sulfoxide (40 mL) was warmed to 40° C. for 15 min and treated with powdered potassium hydroxide (85%, 2.64 g, 40 mmol). The suspension was stirred for 5–10 min and then 1,2,3,4-tetrahydrocyclopent[b]indole (1.57 g, 10 mmol) was added. The suspension was stirred at 40° C. for 60 min, and a solution of (R)-tert-butyl [2-[(1-methanesulfonyl)oxy]propyl]carbamate (6.33 g, 25 mmol) in methyl sulfoxide (13 mL) was added dropwise in portions every 10 min over 90 min. The suspension was stirred at 40° C. for 18 h then cooled to room temperature. Di-tert-butyl dicarbonate (2.3 mL, 2.2 g, 10 mmol) was added and the suspension was stirred for a further 2 h at 20° C. and poured onto a mixture of ice (165 g) and water (55 mL). The suspension was stirred for 1 h and the crude product was collected by filtration, washed with water (2×25 mL) and air-dried for 5 min [alternatively, the work-up employed ethyl acetate extraction of the reaction mixture then column chromatography (SiO$_2$; ethyl acetate-dichloromethane (0:1→1:19)]. The crude product was dissolved in ethyl acetate, dried (magnesium sulfate) and concentrated to give a solid which was triturated with hexane (2.34 g, 74%). Data for (R) 4-[2-(tert-butoxycarbonylamino)-1-propyl]-1,2,3,4-tetrahydrocyclopent[b]indole are listed in Table 4 with data for other products synthesised according to the above method.

TABLE 4

Indole-carbamates synthesised using General Method B

B

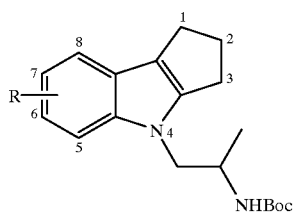

| Example | Compound of formula B | R | Data |
|---|---|---|---|
| 2b, 3b | (2'S)-tert-Butyl[2-[1-[4-(6-chloro-1,2,3,4-tetrahydrocyclo-pent[b]indolyl)]]propyl]-carbamate | 6-Cl (S) | m.p. 172–174° C.; NMR (400 MHz, CDCl$_3$) $\beta_H$ 7.29 (1H, m) 7.29 (1H, d, J 8 Hz), 7.01 (1H, dd, J 1.5, 8 Hz), 4.42 (1H, m, NH), 4.12–3.89 (3H, m), 2.85 (2H, t, J 7 Hz), 2.81 (2H, t, J 7 Hz), 2.52 (2H, quint., J 7 Hz), 1.42 (9H, s), 1.11 (3H, d, J 6.5 Hz). |

TABLE 4-continued

Indole-carbamates synthesised using General Method B

| | | | |
|---|---|---|---|
| 4b, 5b | (2'R)-tert-Butyl[2-[1-[4-(1,2,3,4-tetrahydrocyclopent-[b]indolyl)]]propyl]-carbamate | H (R) | m.p. 170–172° C. (hexane); Found: C, 71.08; H, 8.27; N, 8.71%. $C_{19}H_{26}N_2O_2$. 0.67$H_2O$ requires C, 71.22; H, 8.39; N, 8.74%. |
| 6b, 7b | (2'S)-tert-Butyl[2-[1-[4-(1,2,3,4-tetrahydrocyclopent-[b]indolyl)]]propyl]-carbamate | H (S) | m.p. 172–173° C. (isopropyl ether); Found: C, 71.46; H, 8.22; N, 8.78%. $C_{19}H_{26}N_2O_2$.0.25$H_2O$ requires C, 71.55; H, 8.38; N, 8.78%. |
| 8b, 9b | (2'R)-tert-Butyl[2-[1-[4-(7-fluoro-6-methoxy-1,2,3,4-tetrahydrocyclopent[b]indolyl)]]-propyl]carbamate | 7-F, 6-OMe (R) | Crystallised from EtOH/water (5:1); NMR (400 MHz, CDCl$_3$) $\delta_H$ 7.05 (2H, d, J 12.2 Hz), 4.48–4.34 (1H, m), 4.2–3.98 (2H, m), 3.92 (3H, s, MeO), 3.84 (1H, dd, J 14.0, 7.1 Hz), 2.80 (2H, t, J 7.0 Hz), 2.76 (2H, t, J 7.2 Hz), 2.48 (2H, m), 1.40 (9H, brs), 1.09 (3H, d, J 6.5 Hz); ). HPLC: [Supelcosil ABZ+; 1.0 mL/min, methanol-10 mM aqueous ammonium acetate solution (70:30)] 99% (8.82 min) and [Xterra; 2.0 mL/min, methanol-10 mM aqueous ammonium acetate solution, gradient elution 50% to 80% methanol over the first 4 min, then 80:20] 96% (6.89 min). |
| 10b, 11b | (2'S)-tert-Butyl[2-[1-[4-(6-chloro-7-fluoro-1,2,3,4-tetrahydro | 6-Cl, 7-F (S) | m.p. 173.5–176° C. (hexane); Found: C, 61.45; H, 6.54; N, 7.49%. $C_{19}H_{24}ClFN_2O_2$. 0.25$H_2O$ requires C, 61.45; H, 6.65; N, 7.54%. |
| 12b | (2'S)-tert-Butyl[2-[1-[4-(8-chloro-7-methyl-1,2,3,4-tetra-hydrocyclopent[b]indolyl)]]-propyl]carbamate | 8-Cl, 7-Me (S) | NMR (400 MHz, CDCl$_3$) $\delta_H$ 7.12 (1H, d, J 8 Hz), 6.92 (1H, d, J 8 Hz), 4.40 (1H, m, NH), 4.14 (1H, m), 4.02 (1H, dt, J 6.5, 12 Hz), 3.90 (1H, q, J 7 Hz), 3.06 (2H, t, J 7 Hz), 2.83 (2H, t, J 7 Hz), 2.50 (2H, quintet, J 7 Hz), 2.42 (3H, s), 1.43 (9H, s) and 1.08 (3H, d, J 6.5 Hz); HPLC: [Supelcosil ABZ+; 1.0 ml/min, methanol-10 mM aqueous ammonium acetate solution (80:20)] 98% (8.70 min). |
| 13b | (2'R)-tert-Butyl[2-[1-[4-(8-chloro-7-methyl-1,2,3,4-tetra-hydrocyclopent[b]indolyl)]]-propyl]carbamate | 8-Cl, 7-Me (R) | NMR (400 MHz, CDCl$_3$) $\delta_H$ 7.12 (1H, d, J 8 Hz), 6.91 (1H, d, J 8 Hz), 4.41 (1H, m, NH), 4.12 (1H, m), 4.02 (1H, m), 3.98 (1H, q, J 7 Hz), 3.06 (2H, t, J 7 Hz), 2.82 (2H, t, J 7 Hz), 2.50 (2H, quintet, J 7 Hz), 2.42 (3H, s), 1.43 (9H, s) and 1.08 (3H, d, J 6.5 Hz); HPLC: [Supelcosil ABZ+; 1.0 ml/min, methanol-10 mM aqueous ammonium acetate solution (80:20)] 98% (8.62 min). |
| 14b | (2'R)-tert-Butyl[2-[1-[4-(8-chloro-7-fluoro-1,2,3,4-tetra-hydrocyclopent[b]indolyl)]]-propyl]carbamate | 8-Cl, 7-F (R) | m.p. 160–161° C. (hexane); Found: C, 62.00; H, 6.61; N, 7.56%. $C_{19}H_{24}ClFN_2O_2$ requires C, 62.21; H, 6.59; N, 7.63%. |
| 15b | (2'S)-tert-Butyl[2-[1-[4-(6-chloro-7-fluoro-1,2,3,4-tetra-hydrocyclopent[b]indolyl)]]-propyl]carbamate | 6-Cl, 7-F (S) | NMR (400 MHz, CDCl$_3$) $\delta_H$ 7.17 (1H, m), 6.88 (1H, t, J 9 Hz), 4.40 (1H, m), 4.17 (1H, m), 4.01 (1H, dt, J 7, 12.5 Hz), 3.89 (1H, q, J 7 Hz), 3.05 (2H, t, J 7 Hz), 2.84 (2H, t, J 7 Hz), 2.52 (2H, quintet, J 7 Hz), 1.42 (9H, s) and 1.10 (3H, d, J 6.5 Hz); HPLC: [Supelcosil ABZ+; 1.0 ml/min, methanol-10 mM aqueous ammonium acetate solution (80:20)] 99% (7.63 min). |
| 16b, 17b | (2'R)-tert-Butyl[2-[1-[4-(6-chloro-7-fluoro-1,2,3,4-tetra-hydrocyclopent[b]indolyl)]]-propyl]carbamate | 6-Cl, 7-F (R) | m.p. 176–176.5° C. (hexane); Found: C, 61.71; H, 6.59; N, 7.49%. $C_{19}H_{24}ClFN_2O_2$. 0.25 $H_2O$ requires C, 61.45; H, 6.65; N, 7.54%. |
| 18b, 19b | (2'S)-tert-Butyl[2-[1-[4-(7-chloro-7-fluoro-1,2,3,4-tetra-hydrocyclopent[b]indolyl)]]-propyl]carbamate | 7-F, 6-OMe (S) | NMR (400 MHz, CDCl$_3$) $\delta_H$ 7.08 (1H, br.s), 7.07 (1H, d, J 12 Hz), 4.41 (1H, m, NH), 4.16 (1H, m), 4.12 (1H, m), 3.94 (3H, s), 4.04 (1H, dt, J 6.5, 12 Hz), 3.84 (1H, q, J 7 Hz), 2.80 (4H, m), 2.50 (2H, quintet, J 7 Hz), 1.42 (9H, s), 1.11 (3H, d,16.5 Hz); HPLC: [Xterra; 2.0 ml/min, gradient elution, methanol-10 mM aqueous ammonium acetate solution (50:50) to (80:20) over 4 min then (80:20)] 97% (6.33 min). |
| 20b | (2'S)-tert-Butyl[2-[1-[4-(7-fluoro-8-methoxy-1,2,3,4-tetra-hydrocyclopent[b]indolyl)]]-propyl]carbamate | 7-F, 8-OMe (S) | NMR (400 MHz, CDCl$_3$) $\delta_H$ 6.99–6.94 (1H, m), 6,84 (1H, dd, J 11.3, 9.4 Hz), 4.44–4.37 (1H, m, NH), 4.16–4.00 (2H, m), 4.00 (3H, s), 3.87 (1H, dd, J 14.0, 7.2 Hz), 2.96 (2H, obs t, J 6.6 Hz), 2.83 (2H, obs t, J 7.3 Hz), 2.51 (2H, quintet, J 7.0 Hz), 1.42 (9H, brs), 1.11 (3H, d, J 6.8 Hz); HPLC: [Xterra; 2.0 mL/min, methanol-10 mM aqueous ammonium acetate solution, gradient elution 50% to 80% over the first 4 min, then 80:20] 99.7% (6.55 min). |
| 21b | (2'S)-tert-Butyl[2-[1-[4-(6-methoxy-1,2,3,4-tetrahydrocyclopent[b]indolyl)]]propyl]-carbamate | 6-OMe (S) | NMR (400 MHz, CDCl$_3$) $\delta_H$ 7.28 (1H, d, J 8.5 Hz), 6.94 (1H, m), 6.73 (1H, dd, J 2.5, 8.5 Hz), 4.48 (1H, m, NH), 4.12 (1H, m), 4.05 (1H, m), 3.88 (1H, dd, J 6.5, 14 Hz), 3.87 (3H, s), 2.86–2.78 (4H, m), 2.55–2.46 (2H, m), 1.43 (9H, s), 1.11 (3H, d, J 7 Hz); HPLC: [Supelcosil ABZ+; 1.0 mL/min, methanol-10 mM aqueous ammonium acetate solution (80:20)] 96% (3.87 min). |
| 22b | (2'R)-tert-Butyl[2-[1-[4-(6-methoxy-1,2,3,4-tetrahydrocyclopent[b]indolyl)]]propyl]-carbamate | 6-OMe (R) | NMR (400 MHz, CDCl$_3$) $\delta_H$ 7.28 (1H, d, J 8.5 Hz), 6.92 (1H, m), 6.73 (1H, dd, J 2, 8.5 Hz), 4.44 (1H, m, NH), 4.15–4.01 (2H, m), 3.87 (1H, dd, J 6.5, 14 Hz), 3.86 (3H, s), 2.86–2.77 (4H, m), 2.49 (2H, quint., J 7 Hz), 1.42 (9H, s), 1.11 (3H, d, J 6.5 Hz); HPLC: [Xterra; 2.0 mL/min, methanol-10 mM aqueous ammonium acetate solution, gradient elution 50% to 80% over the first 4 min, then 80:20] 92% (6.00 min). |

Example IV

Reduction of the Indoles to Indolines

The indoles described above in Table 4 were reduced to compounds of formula

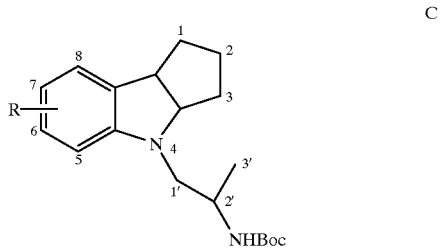

C wherein R represents the substitution pattern consisting of $R^4$, $R^5$, $R^6$ and $R^7$ as defined in formula (I) using the method described above in the synthesis of Example I. Where separable, the indoline diastereoisomers were isolated using flash column chromatography. The appropriate chromatographic systems and the data obtained are described below in Table 5.

TABLE 5

Indoline carbamates synthesised using General Method C

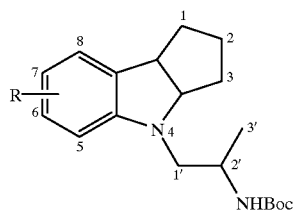

C

| Example | Compound of formula C | R | Data |
|---|---|---|---|
| 2c | (2'S, 3aS, 8bS)-tert-Butyl[2-[1-[4-(6-chloro-1,2,3,3a,4,8b-hexahydrocyclopent-[b]indolyl)-]propyl]-carbamate | 6-Cl (3aS, 8bS) (2'S) | Isomer 1 separated by column chromatography [SiO$_2$; ethyl acetate - heptane (1:10)]; NMR (400 MHz, CDCl$_3$) δ$_H$ 6.82 (1H, dd, J 1, 7.5 Hz), 6.48 (1H, dd, J 2, 7.5 Hz), 6.25 (1H, d, J 2 Hz), 4.28 (2H, m), 3.96 (1H, m), 3.67 (1H, dt, J 3, 9 Hz), 3.18 (1H, q, J 7.5 Hz), 3.01 (1H, dd, J 6.5, 14.5 Hz), 1.95 (1H, m), 1.80 (1H, m), 1.74–1.56 (3H, m), 1.46 (1H, m), 1.37 (9H, s), 1.18 (3H, d, J 6.5 Hz); HPLC: [Supelcosil ABZ+; 1.0 ml/min, methanol-10 mM aqueous ammonium acetate solution (80:20)] 96% (6.24 min); X-ray crystallography showed Example 2c has stereochemistry (3aS, 8bS). |
| 3c | (2'S, 3aR, 8bR)-tert-Butyl[2-[1-[4-(6-chloro-1,2,3,3a,4,8b-hexahydrocyclopent[b]indolyl)-]propyl]carbamate | 6-Cl (3aR, 8bR) (2'S) | Isomer 2 separated by column chromatography [SiO$_2$; ethyl acetate - heptane (1:10)]; NMR (400 MHz, CDCl$_3$) δ$_H$ 6.84 (1H, dd, J 1, 8 Hz), 6.50 (1H, dd, J 2, 8 Hz), 6.26 (1H, d, J 2 Hz), 4.43 (1H, m, NH), 4.21 (1H, m), 3.91 (1H, ddd, J 6.5, 13, 20 Hz), 3.66 (1H, dt J 3, 9 Hz), 3.19 (1H, dd, J 6, 14.5 Hz), 3.04 (1H, dd, J 1, 14.5 Hz), 1.97 (1H, m), 1.84 (1H, m), 1.70 (2H, m), 1.62 (1H, m), 1.49 (1H, m), 1.43 (9H, s), 1.17 (3H, d, 16.5 Hz); HPLC: [OD; 1.0 ml/min, hexane - 2-propanol (95:5)] 96% (7.03 min) |
| 4c | (2'R)-tert-Butyl[2-[1-[4-(1,2,3,3a,4,8b-hexahydrocyclopent[b]indolyl)]]propyl]carbamate isomer I | H (2'R) | Isomer 1. R$_f$ 0.225 [SiO$_2$, isopropyl ether-heptane (2:3)]. NMR (400 MHz, CDCl$_3$) δ$_H$ 6.98 (2H, q, J 7 Hz), 6.56 (1H, t, J 7 Hz), 6.34 (1H, d, J 7 Hz), 4.38 (1H, m, NH), 4.19 (1H, m), 3.94 (1H, m), 3.72 (1H, d, J 3, 9 Hz), 3.21 (1H, q, J 7 Hz), 3.02 (1H, q, J 7 Hz), 1.97 (1H, m), 1.80 (1H, m), 1.70 (2H, m), 1.60 (1H, m), 1.50 (1H, m), 1.40 (9H, s), 1.18 (3H, d, J 7 Hz). |
| 5c | (2'R)-tert-Butyl[2-[1-[4-(1,2,3,3a,4,8b-hexahydrocyclopent[b]indolyl)]]propyl]carbamate isomer II | H (2'R) | Isomer 2. R$_f$ 0.175 [SiO$_2$, isopropyl ether-heptane (2:3)]. NMR (400 MHz, CDCl$_3$) δ$_H$ 6.99 (2H, q, J 7 Hz), 6.58 (1H, t, J 7 Hz), 6.37 (1H, d, J 8 Hz), 4.49 (1H, m, NH), 4.13 (1H, sept, J 3 Hz), 3.92 (1H, sept., J 7 Hz), 3.7 1 (1H, dt, J 3.5, 9 Hz), 3.22 (1H, dd, J 6, 14 Hz), 3.01 (1H, q, 17 Hz), 2.00 (1H, m), 1.83 (1H, m), 1.72 (1H, m), 1.60 (1H, m), 1.52 (1H, m), 1.43 (9H, s), 1.18 (3H, d, J 7 Hz). |
| 6c | (2'S)-tert-Butyl[2-[1-[4-(1,2,3,3a,4,8b-hexahydrocyclopent[b]indolyl)]]propyl]carbamate isomer I | H (2'S) | Isomer 1. m.p 130–133° C.; Found: C, 71.94; H, 8.86; N, 8.79%. C$_{19}$H$_{28}$N$_2$O$_2$ requires C, 72.12; H, 8.92; N, 8.85% |
| 7c | (2'S)-tert-Butyl[2-[1-[4-(1,2,3,3a,4,8b-hexahydrocyclopent[b]indolyl)]]propyl]carbamate isomer II | H (2'S) | Isomer 2. m.p. 92–96° C.. NMR (400 MHz, CDCl$_3$) δ$_H$ 6.98 (2H, q, J 7 Hz), 6.56 (1H, t, J 7 Hz), 6.34 (1H, d, J 7.3 Hz), 4.36 (1H, m, NH), 4.20 (1H, m), 3.94 (1H, m), 3.72 (1H, dt, J 3, 9 Hz), 3.22 (1H, q, J, 7 Hz), 3.02 (1H, q, J 7 Hz), 1.98 (1H, m), 1.81 (1H, m), 1.72 (2H, m), 1.60 (1H, m), 1.49 (1H, m), 1.40 (1H, m), 1.19 (3H, d, J 6.5 Hz). |
| 8c | (2'R)-tert-Butyl[2-[1-[4-(7-fluoro-1,2,3,3a,4,8b-hexa-hydro-6- | 7-F, 6-OMe (2'R) | Isomer 1, column chromatography [SiO$_2$: isopropyl ether-heptane (2:3 to 11:9)]; NMR (400 MHz, CDCl$_3$) δ$_H$ 6.70 (1H, d, J 11.5 Hz), 6.17 (1H, br s), 4.44 (1H, br s), |

TABLE 5-continued

Indoline carbamates synthesised using General Method C

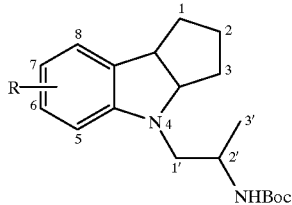

| Example | Compound of formula C | R | Data |
|---|---|---|---|
|  | methoxycyclopent[b]indolyl)]]-propyl]carbamate isomer I |  | 4.10–4.06 (1H, m), 3.88 (1H, obs dd, J 13.6, 7.1 Hz), 3.84 (3H, s, MeO), 3.60 (1H, dt, J 9.1, 3.0), 3.17 (1H, dd, J 13.8, 6.0 Hz), 2.90 (1H, dd, J 13.8, 7.5 Hz), 1.96–1.87 (1H, m), 1.82–1.78 (1H, m), 1.69–1.46 (5H, m), 1.41 (9H, s, tBu), 1.17 (3H, d, J 6.5 Hz). |
| 9c | (2'R)-tert-Butyl[2-[1-[4-(7-fluoro-1,2,3,3a,4,8b-hexa-hydro-6-methoxycyclopent[b]indolyl)]]-propyl]carbamate isomer II | 7-F, 6-OMe (2'R) | Isomer 2; NMR (400 MHz, CDCl$_3$) δ$_H$ 6.68 (1H, d, J 11.2 Hz), 6.07 (1H, d, J 6.0), 4.33 (1H, m), 4.17–4.13 (1H, m), 3.92–3.85 (1H, m), 3.83 (3H, s, MeO), 3.62 (1H, dt, J 8.8, 2.4 Hz), 3.15 (1H, dd, J 14.4, 6.4 Hz), 2.95 (1H, dd, J 14.4, 7.0 Hz), 1.95–1.86 (1H, m), 1.75 (1H, m), 1.69 (5H, m), 1.38 (9H, s, tBu), 1.17 (3H, d, J 6.6). |
| 10c | (2'S)-tert-Butyl[2-[1-[4-(6-chloro-7-fluoro-1,2,3,3a,4,8b-hexahydrocyclopent[b]indolyl)]]-propyl]carbamate isomer I | 6-Cl, 7-F (2'S) | Isomer 1. m.p. 139–143° C.; R$_f$ 0.375 (SiO$_2$, isopropyl ether). NMR (400 MHz, CDCl$_3$) δ$_H$ 6.74 (1H, dd, J 1, 9 Hz), 6.23 (1H, d, J 5.5 Hz), 4.27 (2H, m), 3.94 (1H, m), 3.66 (1H, dt, J 3, 9 Hz), 3.14 (1H, q, J 7 Hz), 2.97 (1H, dd, J 6.5, 14.5 Hz), 1.98 (1H, m), 1.80 (1H, m), 1.67 (2H, m), 1.62 (1H, m), 1.48 (1H, m), 1.37 (9H, s), 1.17 (3H, d, J 6.5 Hz). |
| 11c | (2'S)-tert-Butyl[2-[1-[4-(6-chloro-7-fluoro-1,2,3,3a,4,8b-hexahydrocyclopent[b]indolyl)]]-propyl]carbamate isomer II | 6-Cl, 7-F (2'S) | Isomer 2. R$_f$ 0.325 (SiO$_2$, isopropyl ether). NMR (400 MHz, CDCl$_3$) δ$_H$ 6.75 (1H, dd, J 1, 8 Hz), 6.25 (1H, d, J 6 Hz), 4.40 (1H, m, NH), 4.17 (1H, m), 3.89 (1H, sept., J 7 Hz), 3.64 (1H, dt, J 3, 9 Hz), 3.15 (1H, dd, J 6, 14 Hz), 2.98 (1H, dd, J 6.5, 14.5 Hz), 1.97 (1H, m), 1.82 (1H, m), 1.65 (3H, m), 1.50 (1H, m), 1.42 (9H, s), 1.16 (3H, d, J 6.5 Hz). |
| 12c | (2'S)-tert-Butyl[2-[1-[4-(8-chloro-1,2,3,3a,4,8b-hexahydro-7-methylcyclopent[b]indolyl)]]-propyl]carbamate | 8-Cl, 7-Me (2'R) | Mixture of diastereoisomers; NMR (400 MHz, CDCl$_3$) δ$_H$ 6.83 (1H, t, J 7.5 Hz), 6.23 (0.5H, d, J 7.5 Hz), 6.15 (0.5H, d, J 7.5 Hz), 4.43 (0.5H, m), 4.30 (0.5H, m), 4.22 (0.5H, m), 4.14 (0.5H, m), 3.94 (0.5H, m), 3.89 (0.5H, sextet, J 7 Hz), 3.75 (1H, m), 3.18 (1H, m), 2.96 (1H, m), 2.23 (1.5H, s), 2.22 (1.5H, s), 2.04 (1H, m), 1.84 (1H, m), 1.72 (1H, m), 1.62 (1H, m), 1.54 (1H, m), 1.42 (4.5H, s), 1.37 (4.5H, s), 1.17 (1.5H, d, J 6.5 Hz) and 1.16 (1.5H, d, J 6.5 Hz); HPLC: [Supelcosil ABZ+; 1.0 ml/min, methanol-10 mM aqueous ammonium acetate solution (80:20)] 47% (7.86 min) and 41% (8.54 min). |
| 13c | (2'R)-tert-Butyl[2-[1-[4-(8-chloro-1,2,3,3a,4,8b-hexahydro-7-methylcyclopent[b]indolyl)]]-propyl]carbamate | 8-Cl, 7-Me (2'R) | Mixture of diastereoismers; NMR (400 MHz, CDCl$_3$) δ$_H$ 6.83 (1H, t, J 7.5 Hz), 6.23 (0.5H, d, J 7.5 Hz), 6.15 (0.5H, d, J 7.5 Hz), 4.43 (0.5H, m), 4.30 (0.5H, m), 4.22 (0.5H, m), 4.14 (0.5H, m), 3.94 (0.5H, m), 3.89 (0.5H, sextet, J 7 Hz), 3.75 (1H, m), 3.18 (1H, m), 2.96 (1H, m), 2.23 (1.5H, s), 2.22 (1.5H, s), 2.04 (1H, m), 1.84 (1H, m), 1.72 (1H, m), 1.62 (1H, m), 1.54 (1H, m), 1.42 (4.5H, s), 1.37 (4.5H, s), 1.17 (1.5H, d, J 6.5 Hz) and 1.16 (1.5H, d, J 6.5 Hz); HPLC: [Supelcosil ABZ+; 1.0 ml/min, methanol-10 mM aqueous ammonium acetate solution (80:20)] 52% (7.97 min) and 41% (8.68 min). |
| 14c | (2'R)-tert-Butyl[2-[1-[4-(8-chloro-7-fluoro-1,2,3,3a,4,8b-hexahydrocyclopent[b]indolyl)]]-propyl]carbamate | 8-Cl, 7-F (2'R) | Mixture of diastereoisomers; m.p. 106–114° C.; NMR (400 MHz, CDCl$_3$) δ$_H$ 6.78 (0.5H, t, J 8 Hz), 6.76 (0.5H, t, J 8 Hz), 6.20 (0.5H, dd, J 3, 8.5 Hz), 6.11 (0.5H, dd, J 3.5, 8 Hz), 4.40 (0.5H, m), 4.28 (1H, m), 4.18 (0.5H, m), 3.94 (0.5H, m), 3.89 (0.5H, sept., J 7 Hz), 3.75 (1H, app. dq, J 3.5, 9 Hz), 3.21 (0.5H, dd, J 6, 14.5 Hz), 3.16 (0.5H, q, J 7 Hz), 2.03 (1H, m), 1.84 (2H, m), 1.72 (1H, m), 1.64 (1H, m), 1.53 (1H, m), 1.43 (4.5H, s), 1.38 (4.5H, s), 1.16 (3H, d, J 7Hz). |
| 15c | (2'S)-tert-Butyl[2-[1-[4-(8-chloro-7-fluoro-1,2,3,3a,4,8b-hexahydrocyclopent[b]indolyl)]]-propyl]carbamate | 8-Cl, 7-F (2'S) | Mixture of diastereoisomers; NMR (400 MHz, CDCl$_3$) δ$_H$ 6.78 (0.5H, t, J 8 Hz), 6.75 (0.5H, t, J 8.5 Hz), 6.20 (0.5H, dd, J 3, 8.5 Hz), 6.10 (0.5H, dd, J 3.5, 8.5 Hz), 4.40 (0.5H, m), 4.28 (1H, m), 4.17 (0.5H, m), 3.94 (0.5H, m), 3.89 (0.5H, sept., J 7 Hz), 3.78 (0.5H, dd, J 3.5, 9.5 Hz), 3.73 (0.5H, dd, J 4, 9 Hz), 3.20 (0.5, dd, J 5.5, 14 Hz), 3.16 (0.5H, q, J 7 Hz), 2.97 (0.5H, q, J 7 Hz), 2.91 (0.5H, q, J 7 Hz), 2.03 (1H, m), 1.84 (2H, m), 1.73 (1H, m), 1.64 (1H, m), 1.54 (1H, m), 1.43 (4.5H, s), 1.37 (4.5H, s), 1.16 (3H, d, J 6.5 Hz); HPLC: [Xterra 2.0 ml/min, gradient elution, methanol-10 mM aqueous ammonium acetate solution (50:50) to (80:20) over 4 min then (80:20)] 51% (7.79 min) and 48% (7.95 min). |
| 16c | (2'R)-tert-Butyl[2-[1-[4-(6-chloro-7-fluoro-1,2,3,3a,4,8b-hexahydrocyclopent[b]indolyl)]]-propyl]carbamate isomer I | 6-Cl, 7-F (2'R) | Isomer 1. R$_f$ 0.15 [SiO$_2$, isopropyl ether-heptane (2:3)]. NMR (400 MHz, CDCl$_3$) δ$_H$ 6.74 (1H, dd, J 1, 8.5 Hz), 6.23 (1H, d, J 5.5 Hz), 4.26 (2H, m), 3.94 (1H, m), 3.36 (1H, dt, J 3, 6 Hz), 3.14 (1H, q, J 7 Hz), 2.98 (1H, dd, J 6, 14 Hz), 1.96 (1H, m), 1.78 (1H, m), 1.68 (2H, m), 1.62 (1H, m), 1.48 (1H, m), 1.37 (1H, m), 1.37 (2H, d, J 6.5 Hz). |
| 17c | (2'R)-tert-Butyl[2-[1-[4-(6-chloro-7-fluoro-1,2,3,3a,4,8b-hexahydrocyclopent[b]indolyl)]]-propyl]carbamate isomer II | 6-Cl, 7F (2'R) | Isomer 2. R$_f$ 0.10 [SiO$_2$, isopropyl ether-heptane (2:3)]. NMR (400 MHz, CDCl$_3$) δ$_H$ 6.76 (1H, dd, J 1, 8.5 Hz), 6.25 (1H, d, J 6 Hz), 4.41 (1H, m, NH), 4.17 (1H, dt, J 2.5, 6.5 Hz), 3.89 (1H, sept., J 7 Hz), 3.65 (1H, dt, J 3, 9 Hz), 3.16 (1H, dd, J 6, 14.5 Hz), 2.98 (1H, q, J 7 Hz), 1.97 (1H, m), 1.82 (1H, m), 1.68 (1H, m), 1.61 (1H, m), 1.43 (9H, s), 1.17 (3H, d, J 6.5 Hz). |
| 18c | (2'S)-tert-Butyl[2-[1-[4-(7-fluoro-1,2,3,3a,4,8b-hexa-hydro-6-methoxy-cyclopent[b]indolyl)]]-propyl]carbamate isomer I | 7-F, 6-OMe (2'S) | Isomers were partially separated by column chromatography [SiO$_2$: isopropyl ether-heptane (1:3)–(2:5)] and used in the next step without further purification or analysis. |
| 19c | (2'S)-tert-Butyl[2-[1][4-(7-fluoro-1,2,3,3a,4,8b-hexa-hydro-6-methoxy-cyclopent[b]indolyl)]]- | 7-F, 6-OMe (2'S) | Isomer 2, as Example 18. |

TABLE 5-continued

Indoline carbamates synthesised using General Method C

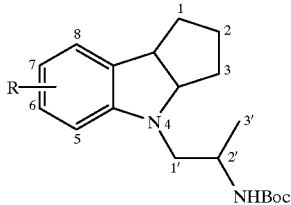

C

| Example | Compound of formula C | R | Data |
|---|---|---|---|
| | propyl]carbamate isomer II | | |
| 20c | (2'S)-tert-Butyl[2-[1-[4-(7-fluoro-1,2,3,3a,4,8b-hexa-hydro-8-methoxy-cyclopent[b]indolyl)]]-propyl]carbamate | 7-F, 8-OMe (2'S) | Mixture of diastereoisomers; NMR (400 MHz, CDCl$_3$) δ$_H$ 6.77–6.70 (1H, m), 6.00 (0.5H, dd, J 8.5, 3.1 Hz), 5.92 (0.5H, dd, J 8.5, 3.0 Hz), 4.44–4.40 (0.5H, m), 4.38–4.28 (0.5H, m), 4.22–4.19 (0.5H, m), 4.16–4.09 (0.5H, m), 3.94 (1.5H, s, MeO), 3.93 (1.5H, s, MeO), 3.89–3.84 (1H, m), 3.80–3.72 (1H, dq, J 8.7, 3.6 Hz), 3.18 (0.5H, dd, J 14.1, 6.7 Hz), 3.13 (0.5H, dd, J 14.7, 7.0 Hz), 2.97 (0.5H, dd, J 14.4, 7.0 Hz), 2.90 (0.5H, dd, J 14.1, 7.2), 2.06–1.95 (1H, m), 1.82–1.52 (5H, m), 1.44 (9H, s, tBu), 1.17 (3H, d, J 6.5); HPLC: [Xterra 2.0 ml/min, gradient elution, methanol-10 mM aqueous ammonium acetate solution (50:50) to (80:20) over 4 min then (80:20)] 52% (6.90 min) and 46% (7.06 min). |
| 21c | (2'S)-tert-Butyl[2-[1-[4-(1,2,3,3a,4,8b-hexahydro-6-methoxycyclopent[b]indolyl)]]-propyl]carbamate | 6-OMe (2'S) | Mixture of diastereoisomers. m.p. 128–144° C.; NMR (400 MHz, CDCl$_3$) δ$_H$ 6.86 (0.5H,dd, J 1, 8 Hz), 6.84 (0.5H, dd, J 1, 8 Hz), 6.11 (0.5H, dd, J 2.5, 8 Hz), 6.09 (0.5H, dd, J 2.5, 8 Hz), 5.97 (0.5H, m), 5.94 (0.5H, d, J 2.5 Hz), 4.45 (0.5H, m, NH), 4.35 (0.5H, m, NH), 4.22 (0.5H, ddd, J 2.5, 6.5, 8.5 Hz), 4. 17 (0.5H, ddd, J 2.5, 6, 8.5 Hz), 3.92 (1H, m), 3.75 (3H, s), 3.65 (1H, m), 3.21 (0.5H, dd, J 6, 14 Hz), 3.18 (0.5H, dd, J 6.5, 14 Hz), 3.01 (0.3H, dd, J 7.5, 14 Hz), 3.005 (0.5H, q, J 7 Hz), 1.93 (1H, m), 1.81 (1H, m), 1.69 (2H, m), 1.59 (1H, m), 1.5O (1H, m), 1.43 (4.5H, s), 1.40 (4.5H, s), 1.18 (1.5H, d, J 6.5 Hz), 1.17 (1.5H, d, J 6.5 Hz). |
| 22c | (2'R)-tert-Butyl[2-[1-[4-(1,2,3,3a,4,8b-hexahydro-6-methoxycyclopent[b]indolyl)]]-propyl]carbamate | 6-OMe (2'R) | Mixture of diastereoisomers. R$_f$ 0.45 (SiO$_2$, isopropyl ether); NMR (400 MHz, CDCl$_3$) δ$_H$ 6.86 (0.5H, dd, J 1, 8 Hz), 6.84 (0.5H, dd, J 1.5, 8 Hz), 6.11 (0.5H, dd, J 2.5, 8 HZ), 6.09 (0.5H, dd, J 2.5, 8 Hz), 5.97 (0.5H, m), 5.94 (0.5H, d, J 2.5Hz), 4.45 (0.5H, m, NH), 4.35 (0.5H, m, NH), 4.22 (0.5H, m), 4.17 (0.5H, m), 4.00–3.85 (1H, m), 3.75 (3H, s), 3.65 (1H, app. tt, J 3, 9 Hz), 3.21 (0.5H, dd, J 6.5, 14 Hz), 3.18 (0.5H, q, J 7 Hz), 3.01 (0.5H, q, J 7 Hz), 3.00 (0.5H, q, J 7 Hz), 1.94 (1H, m), 1.81 (1H, m), 1.69 (2H, m), 1.59 (1H, m), 1.50 (1H, m), 1.43 (4.5H, s), 1.40 (4.5H, s), 1.18 (1.5H, d, J 6.5 Hz), 1.17 (1.5H, d, J 6.5 Hz). |

Example V

Deprotection of the Boc-indolines

The indolines were deprotected using the method described above in the synthesis of Example 1. Data obtained for the products of formula D wherein R represents the substitution pattern consisting of R$^4$, R$^5$, R$^6$ and R$^7$ as defined in formula (I)

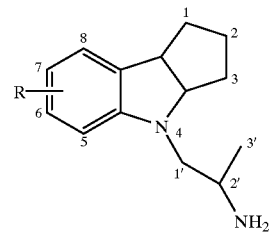

D are described below in Table 6.

TABLE 6

Indolines synthesised using General Method D.

[Structure D: tricyclic indoline with cyclopentane fused ring system, positions labeled 1,2,3,3a,4,5,6,7,8,8b and N4, with N-substituent -CH(1')-CH(2')(CH3 3')-NH2; R group on aromatic ring at position 6/7]

| Example | Product of formula D | R | Yield | Data |
|---|---|---|---|---|
| 2 | (2'S, 3aS, 8b5)-[1-[4-(6-Chloro-1,2,3,3a,4,8b-hexahydrocyclopent-[b]indolyl)]-2-propylamine hydrochloride | 6-Cl (3aS, 8bS) (2'S) | 83% | HCl. NMR 400 MHz (DMSO-$d_6$) $\delta_H$ 8.11 (3H, m, —$NH_3^+$), 6.95 (1H, d, J 7.5 Hz), 6.52 (1H, dd, J 1.5, 7.5 Hz), 6.49 (1H, d, J 1.5 Hz), 4.27 (1H, ddd, J 2.5, 5.5, 8.5 Hz), 3.69 (1H, dt, J 2.5, 9 Hz), 3.45 (1H, t, J 7.5 Hz), 3.42 (1H, dd, J 7.5, 7 Hz), 3.21 (dt, J 4.5, 17 Hz), 1.97 (1H, m), 1.78–1.54 (4H, m), 1.35 (1H, m), 1.27 (3H, d, J 6.5 Hz); HPLC: [Supelcosil ABZ+; 1.0 ml/min, methanol-10 mM aqueous ammonium acetate solution (80:20)] 96% (3.41 min). |
| 3 | (2'S, 3aR, 8bR)-1-[4-(6-Chloro-1,2,3,3a,4,8b-hexahydrocyclopent-[b]indolyl)]-2-propylamine hydrochloride | 6-Cl (3aR, 8bR) (2'S) | 100% | HCl. $C_{14}H_{19}ClN_2$ requires MH$^+$ 251, 253. Found m/z 251, 253; HPLC: [Supelcosil ABZ+; 1.0 ml/min, methanol-10 mM aqueous ammonium acetate solution (80:20)] 97% (3.49 min). |
| 4 | (2'R)-1-[4-(1,2,3,3a,4,8b-Hexahydrocyclopent[b]indolyl)]-2-propylamine isomer I fumarate | H (2'R) | 70% | Isomer 1; fumarate; NMR 400 MHz (DMSO-$d_6$) $\delta_H$ 6.97 (1H, d, J 7.5 Hz), 6.95 (1H, t, J 8 Hz), 6.54 (1H, t, J 7 Hz), 6.46 (2H, s), 6.42 (1H, d, J 8 Hz), 4.17 (1H, sept., J 3 Hz), 3.70 (1H, dt, J 2.5, 8.5 Hz), 3.40 (1H, sextet, J 6.5 Hz), 3.30 (1H, q, J 7 Hz), 3.15 (1H, q, J 7 Hz), 2.00 (1H, m), 1.78–1.54 (4H, m), 1.40 (1H, m), 1.22 (3H, d, J 6.5 Hz); HPLC: [Xterra; 2.0 ml/min, methanol-10 mM aqueous ammonium acetate solution (50:50) to (80:20) over 4 min then (80:20)] 94% (1.25 min). |
| 5 | (2'R)-1-[4-(1,2,3,3a,4,8b-Hexahydrocyclopent[b]indolyl)]-2-propylamine isomer II fumarate | H (2'R) | 91% | Isomer 2; fumarate; NMR 400 MHz (DMSO-$d_6$) $\delta_H$ 6.97 (1H, d, J 7 Hz), 6.95 (1H, t, J 8 Hz), 6.54 (1H, dt, J 1, 7 Hz), 6.46 (2H, s), 6.43 (1H, t, J 8 Hz), 4.16 (1H, sept., J 3 Hz), 3.70 (1H, dt, J 3, 9 Hz), 3.40 (1H, sextet, J 7 Hz), 3.27 (1H, q, J 7 Hz), 3.1 7 (1H, q, J 7 Hz), 1.98 (1H, m), 1.79–1.54 (4H, m), 1.40 (1H, m), 1.19 (3H, d, J 6.5 Hz); HPLC: [Xterra; 2.0 ml/min, methanol-10 mM aqueous ammonium acetate solution (50:50) to (80:20) over 4 min then (80:20)] 98% (1.36 min). |
| 6 | (2'S)-1-[4-(1,2,3,3a,4,8b-Hexahydrocyclopent[b]indolyl)]-2-propylamine isomer I fumarate | H (2'S) | 58% | Isomer 1; fumarate; NMR 400 MHz (DMSO-$d_6$) $\delta_H$ 6.97(1H,d, J 7 Hz),6.94 (1H, d, J 8 Hz), 6.54 (1H, t, J 7 Hz), 6.46 (2H, s), 6.42 (1H, t, J 8 Hz), 4.17 (1H, sept., J 3 Hz), 3.70 (1H, dt, J 2.5, 8.5 Hz), 3.39 (1H, sext., J 6.5 Hz), 3.31 (1H, dd, J 7, 14 Hz), 3.15 (1H, q, J 7 Hz), 1.99 (1H, m), 1.78–1.54 (4H, m), 1.40 (1H, m), 1.22 (3H, d, J 6.5 Hz); HPLC: [Xterra; 2.0 ml/min, methanol-10 mM aqueous ammonium acetate solution (50:50) to (80:20) over 4 min then (80:20)] 97% (1.18 min). |
| 7 | (2'S)-1-[4-(1,2,3,3a,4,8b-Hexahydrocyclopent[b]indolyl)]-2-propylamine isomer II fumarate | H (2'S) | 60% | Isomer 2; fumarate; NMR 400 MHz (DMSO-$d_6$) $\delta_H$ 6.97 (1H, d, J 7 Hz), 6.95 (1H, t, J 8 Hz), 6.54 (1H, t, J 7.5 Hz), 6.46 (2H, s), 6.43 (1H, t, J 8 Hz), 4.16 (1H, sept., J 3 Hz), 3.70 (1H, dt, J 2.5, 9 Hz), 3.40 (1H, app. sextet, J 6.5 Hz), 3.27 (1H, q, J 7 Hz), 3.17 (1H, q, 17 Hz), 1.99 (1H, m), 1.80–1.54 (4H, m), 1.41 (1H, m), 1.19 (3H, d, J 6.5 Hz); HPLC: [Xterra; 2.0 ml/min, methanol-10 mM aqueous ammonium acetate solution (50:50) to (80:20) over 4 min then (80:20)] 98% (0.92 min). |
| 8 | (2'R)-1-[4-(7-Fluoro-1,2,3,3a,4,8b-hexahydro-6-methoxycyclopent-[b]indolyl)]-2-propylamine isomer I fumarate | 7-F, 6-OMe (2'R) | 67% | Isomer 1; fumarate; NMR 400 MHz (DMSO-$d_6$) $\delta_H$ 6.84 (1H, d, J 9.1 Hz), 6.46 (2H, s), 6.37 (1H, d, J 7.7 Hz), 4.12 (1H, ddd, J 8.8, 6.1, 2.7 Hz), 3.78 (3H, s, MeO), 3.65 (1H, dt, J 8.6, 2.6 Hz), 3.41–3.36 (1H, m), 3.30 (1H, dd, J 13.9, 8.1), 3.16 (1H, dd, J 13.9, 6.0 Hz), 1.94–1.89 (1H, m), 1.75–1.43 (4H, m), 1.20 (3H, d, J 6.4 Hz); HPLC: [Xterra; 2.0 ml/min, methanol-10 mM aqueous ammonium acetate solution (50:50) to (80:20) over 4 min then (80:20)] 100% (1.13 min). |
| 9 | (2'R)-1-[4-(7-Fluoro-1,2,3,3a,4,8b-hexahydro-6-methoxycyclopent-[b]indolyl)]-2-propylamine isomer II hemifumarate | 7-F, 6-OMe (2'R) | 57% | Isomer 2; hemifumarate; NMR 400 MHz (DMSO-$d_6$) $\delta_H$ 6.82 (1H, d, J 11.5 Hz), 6.41 (1H, s), 6.22 (1H, d, J 7.1 Hz), 4.17 (1H, obs dt, J 6.1, 2.5 Hz), 3.78 (3H, s, MeO), 3.64 (1H, dt, J 8.5, 2.5 Hz), 3.30–3.25 (1H, m), 3.18 (1H, dd, J 14.0, 7.5 Hz), 3.05 (1H, dd, J 14.0, 6.4 Hz), 1.94–1.89 (1H, m), 1.75–1.73 (1H, m), 1.67–1.55 (3H, m), 1.40–1.36 (1H, m), 1.16 (3H, d, J 6.1 Hz); HPLC: [Xterra; 2.0 ml/min, methanol-10 mM aqueous ammonium acetate solution (50:50) to (80:20) over 4 min then (80:20)] 97% (1.27 min). |
| 10 | (2'S)-1-[4-(6-Chloro-7-fluoro-1,2,3,3a,4,8b-hexahydrocyclopent-[b]indolyl)]-2-propylamine isomer I fumarate | 6-Cl, 7-F (2'S) | 47% | Isomer 1; fumarate; NMR 400 MHz (DMSO-$d_6$) $\delta_H$ 7.04 (1H, dd, J 1, 9 Hz), 6.58 (1H, d, J 6 Hz), 6.46 (2H, s), 4.21 (1H, ddd, J 2.5, 6, 9 Hz), 3.69 (1H, dt, J 3, 9 Hz), 3.57 (1H, sept., 17 Hz), 3.23 (1H, dd, J 8, 14.5 Hz), 3.17 (1H, dd, J 6.5, 14.5 Hz), 1.96 (1H, m), 1.74 (1H, m), 1.66 (2H, m), 1.57 (1H, m), 1.41 (1H, m), 1.18 (3H, d, J 6.5 Hz); HPLC: [Xterra; 2.0 ml/min, methanol-10 mM aqueous ammonium acetate solution (50:50) to (80:20) over 4 min then (80:20)] 97% (2.70 min). |
| 11 | (2'S)-1-[4-(6-Chloro-7-fluoro-1,2,3,3a,4,8b-hexahydrocyclopent-[b]indolyl)]-2-propylamine isomer I fumarate | 6-Cl, 7-F (2'S) | 59% | Isomer 2; hemifumarate; NMR 400 MHz (DMSO-$d_6$) $\delta_H$ 7.02 (1H, dd, J 1, 8.5 Hz), 6.46 (1H, d, J 6 Hz), 6.42 (1H, s), 4.24 (1H, m), 3.69 (1H, dd, J 2, 8.5 Hz), 3.26 (1H, sextet, J 6.5 Hz), 3.17 (1H, q, J 7 Hz), 3.03 (1H, dd, J 6.5, 14 Hz), 1.96 (1H, m), 1.77 (1H, m), 1.70–1.55 (3H, m), 1.36 (1H, m), 1.13 (3H, d, 16.5 Hz); HPLC: [Xterra; 2.0 ml/min, methanol-10 mM aqueous ammonium |

TABLE 6-continued

Indolines synthesised using General Method D.

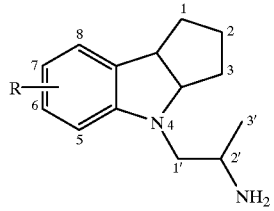

D

| Example | Product of formula D | R | Yield | Data |
|---|---|---|---|---|
| 12 | (2'S)-[1-[4-(8-Chloro-1,2,3,3a,4,8b-hexahydro-7-methyl-cyclopent[b]-2-propylamine fumarate | 8-Cl, 7-Me (2'S) | 43% | acetate solution (50:50) to (80:20) over 4 min then (80:20)] 96% (2.45 min). Mixture of diastereoisomers; fumarate; m.p. 167–170° C. (dec.); NMR 400 MHz (DMSO-d$_6$) δ$_H$ 6.93 (1H, d, J 8 Hz), 6.47 (2H, s), 6.36 (0.5H, d, 18 Hz), 6.32 (0.5H, d, J 8 Hz), 4.21 (1H, m), 3.71 (1H, dt, J 3.5, 9 Hz), 3.39 (1H, m), 3.31 (0.5H, q, J 3.5 Hz), 3.27 (0.5H, q, J 3.5 Hz), 3.18 (0.5H, dd, J 3, 7.5 Hz), 3.14 (0.5H, dd, J 3, 7.5 Hz), 2.18 (3H, s), 2.12 (1H, m), 1.74 (3H, m), 1.60 (1H, m), 1.46 (1H, m), 1.21 (1.5H, d, J 6.5 Hz) and 1.17 (1.5H, d, J 6.5 Hz). |
| 13 | (2'R)-[1-[4-(8-Chloro-1,2,3,3a,4,8b-hexahydro-7-methyl-cyclopent[b]-2-propylamine fumarate | 8-Cl, 7-Me (2'S) | 10% | Mixture of diastereoisomers; fumarate; m.p. 160–165° C. (dec.); NMR 400 MHz (DMSO-d$_6$) δ$_H$ 6.93 (1H, d, J 8 Hz), 6.47 (2H, s), 6.36 (0.5H, d, J 8 Hz), 6.32 (0.5H, d, J 8 Hz), 4.21 (1H, m), 3.71 (1H, dt, J 3.5, 9 Hz), 3.39 (1H, m), 3.31 (0.5H, q, J 3.5 Hz), 3.27 (0.5H, q, J 3.5 Hz), 3.18 (0.5H, dd, J 3, 7.5 Hz), 3.14 (0.5H, dd, J 3, 7.5 Hz), 2.18 (3H, s), 2.12 (1H, m), 1.74 (3H, m), 1.60 (1H, m), 1.46 (1H, m), 1.21 (1.5H, d, J 6.5 Hz) and 1.17 (1.5H, d, J 6.5 Hz). |
| 14 | (2'R)-[1-[4-(8-Chloro-7-fluoro-1,2,3,3a,4,8b-hexahydro-cyclopent[b]indolyl)]-2-propylamine fumarate | 8-Cl, 7-F (2'R) | 50% | Mixture of diastereoisomers; fumarate; NMR 400 MHz (DMSO-d$_6$); δ$_H$ 6.99 (0.5H, t, J 9 Hz), 6.98 (0.5H, t, J 9 Hz), 6.46 (2H, s), 6.40 (0.5H, dd, J 3.5, 8.5 Hz), 6.36 (0.5H, J 3.5, 8.5 Hz), 4.26 (1H, m), 3.76 (1H, dt, J 4, 9 Hz), 3.38 (1H, sextet, J 6.5 Hz), 3.29 (1H, q, J 17 Hz), 3.16 (0.5H, dd, J 6.5, 14.5 Hz), 3.15 (0.5H, dd, J 6.5, 14 Hz), 2.04 (1H, m), 1.83–1.67 (3H, m), 1.61 (1H, m), 1.48 (1H, m), 1.21 (1.5H, d, J 6.5 Hz), 1.17 (1.5H, d, J 6.5 Hz); HPLC: [Xterra; 2.0 ml/min, methanol-10 mM aqueous ammonium acetate solution (50:50) to (80:20) over 4 min then (80:20)] 95% (3.03 min). |
| 15 | (2'S)-[1-[4-(8-Chloro-7-fluoro-1,2,3,3a,4,8b-hexahydro-cyclopent[b]indolyl)]-2-propylamine fumarate | 8-Cl, 7-F (2'S) | 61% | Mixture of diastereoisomers; fumarate; NMR 400 MHz (DMSO-d$_6$); δ$_H$ 6.982 (0.5H, t, J 9 Hz), 6.978 (0.5H, t, J 9 Hz), 6.47 (2H, s), 6.41 (0.5H, dd, J 4, 9 Hz), 6.36 (0.5H, dd, J 3.5, 9 Hz), 4.26 (1H, dt, J 5, 9 Hz), 3.76 (1H, dt, J 4, Hz), 3.39 (1H, q, J 6.5 Hz), 3.29 (1H, q, J 7.5 Hz), 3.17 (1H, q, J 17.5 Hz), 2.04 (1H, app. tdd, J 3, 6.5, 9 Hz), 1.74 (3H, m), 1.61 (1H, sept., J 5.5 Hz), 1.47 (1H, m), 1.22 (1.5H, d, J 6.5 Hz) 1.18 (1.5H, d, J 6.5 Hz); HPLC: [Xterra; 2.0 ml/min, methanol-10 mM aqueous ammonium acetate solution (50:50) to (80:20) over 4 min then (80:20)] 98% (3.76 min). |
| 16 | (2'R)-1-[4-(6-Chloro-7-fluoro-1,2,3,3a,4,8b-hexahydro-cyclopent[b]indolyl)]-2-propylamine isomer I fumarate | 6-Cl, 7-F (2'R) | 46% | Isomer 1; fumarate; NMR 400 MHz (DMSO d$_6$); δ$_H$ 7.03 (1H, dd, J 1, 8.5 Hz), 6.52 (1H, d, 6 Hz), 6.47 (2H, s), 4.25 (1H, sept., J 3 Hz), 3.69 (1H, dt, J 2.5, 9 Hz), 3.38 (1H, sextet, J 6 Hz), 3.31 (1H, q, J 7 Hz), 3.13 (1H, dd, J 6.5, 14.5 Hz), 1.97 (1H, m), 1.80–1.54 (4H, m), 1.2 (1H, m), 1.21 (3H, d, J 6.5 Hz); HPLC: [Xterra; 2.0 ml/min, methanol-10 mM aqueous ammonium acetate solution (50:50) to (80:20) over 4 min then (80:20)] 99% (2.75 min). |
| 17 | (2'R)-1-[4-(6-Chloro-7-fluoro-1,2,3,3a,4,8b-hexahydro-cyclopent[b]indolyl)]-2-propylamine isomer II fumarate | 6-Cl, 7-F (2'R) | 44% | Isomer 2; fumarate; NMR 400 MHz (DMSO-d$_6$); δ$_H$ 7.04 (1H, dd, J 1, 9 Hz), 6.59 (1H, d, J Hz), 6.47 (2H, s), 4.21 (ddd, J 2.5, 6, 8.5 Hz), 3.70 (1H, dt, J 2.5, 8.5 Hz), 3.38 (1H, q, J 7, 13, 19 Hz), 3.25 (1H, dd, J 7.5, 14 Hz), 3.18 (dd, J 6.5, 14 Hz), 1.96 (1H, m), 1.74 (1H, m), 1.67 (2H, m), 1.58 (1H, m), 1.42 (1H, m), 1.1 (3H, d, J 6.5 Hz); HPLC: [Xterra; 2.0 ml/min, methanol-10 mM aqueous ammonium acetate solution (50:50) to (80:20) over 4 min then (80:20)] 99% (2.91 min). |
| 18 | (2'S)-1-[4-(7-Fluoro-1,2,3,3a,4,8b-hexahydro-6-methoxycyclopent[b]indolyl)]-2-propylamine isomer I 0.7 fumarate | 7-F, 6-OMe (2'S) | 50% | Isomer 1; 0.7 fumarate; NMR 400 MHz (DMSO-d$_6$) δ$_H$ 6.81 (1H, d, J 10.0 Hz), 6.41 (1.4H, s), 6.32 (1H, d, J 7.0 Hz), 4.10 (1H, ddd, J 9.1, 6.0, 2.5 Hz), 3.76 (3H, s, MeO), 3.63 (1H, dt, J 9.1, 2.7 Hz), 3.32–3.29 (1H, m), 3.22 (1H dd, J 14.0, 7.0 Hz), 3.10 (1H, dd, J 14.0, 6.0 Hz), 1.94–1.85 (1H, m), 1.75–1.52 (3H, m), 1.48–1.38 (1H, m), 1.15 (3H, d, J 6.4 Hz); HPLC: [Xterra; 2.0 ml/min, methanol-10 mM aqueous ammonium acetate solution (50:50) to (80:20) over 4 min then (80:20)] 100% (1.2 min). |
| 19 | (2'S)-1-[4-(7-Fluoro-1,2,3,3a,4,8b-hexahydro-6-methoxycyclopent[b]indolyl)]-2-propylamine isomer I 0.7 fumarate | 7-F, 6-OMe (2'S) | 68% | Isomer 2; 0.7 fumarate; NMR 400 MHz (DMSO-d$_6$) δ$_H$ 6.83 (1H, d, J 11.0 Hz), 6.43 (1.4H, s), 6.28 (1H, d, J 7.0 Hz), 4.18 (1H, ddd, J 8.7, 6.1, 2.8 Hz), 3.78 (3H, s, MeO), 3.64 (1H, dt, J 8.8, 2.8 Hz), 3.38–3.23 (2H, m), 3.12 (1H, dd, J 13.5, 6.6 Hz), 1.97–1.88 (1H, m), 1.75–1.54 (3H, m), 1.43–1.33 (1H, m), 1.21 (3H, d, J 6.6 Hz); HPLC: [Xterra; 2.0 ml/min, methanol-10 mM aqueous ammonium acetate solution (50:50) to (80:20) over 4 min then (80:20)] 98% (1.51 min). |
| 20 | (2'S)-[1-[4-(7-Fluoro-1,2,3,3a,4,8b-hexahydro-8-methoxycyclopent[b]indolyl)]-2-propylamine fumarate | 7-F, 8-OMe (2'R) | 48% | Mixture of diastereoisomers, fumarate: NMR 400 MHz (DMSO-d$_6$) δ$_H$ 687–682 (1H, m), 6.45 (2H, s), 6.14 (0.5H, dd, J 8.8, 3.1 Hz), 6.08 (0.5H, dd, J 8.5, 3.6 Hz), 4.20–4.14 (1H, m), 3.85 (3H, s, MeO), 3.79–3.73 (1H, m), 3.41–3.33 (1H, m), 3.28–3.21 (1H, m), 3.14–3.06 (1H, m), 2.04–1.94 (1H, m), 1.77–1.54 (3H, m), 1.52–1.42 (1H, m), 1.20 (1.5H, d, J 6.5 Hz), 1.17 (1.5H, d, J 6.5 Hz); HPLC: [Xterra; 2.0 ml/min, methanol-10 mM aqueous ammonium acetate solution (50:50) to (80:20) over 4 min then (80:20)] 98% (1.60 min). |

TABLE 6-continued

Indolines synthesised using General Method D.

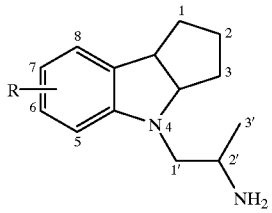

D

| Example | Product of formula D | R | Yield | Data |
|---|---|---|---|---|
| 21 | (2'R)-[1-[4-(1,2,3,3a,4,8b-hexahydro-6-methoxycyclopent-[b]indolyl)]-2-propylamine fumarate | 6-OMe (2'R) | 32% | Mixture of diastereoisomers; fumarate: NMR 400 MHz (DMSO-d$_6$) δ$_H$ 6.83 (1H, dd, J 2.5, 7.5 Hz), 6.46 (2H, s), 6.11–6.06 (1.5H, m), 6.04 (0.5H, d, J 2 Hz), 4.19 (1H, m), 3.68 (3H, s), 3.63 (1H, dt, J 2.5, 9 Hz), 3.44–3.11 (4H, m), 1.93 (1H, m), 1.73 (1H, m), 1.63–1.52 (3H, m), 1.40 (1H, m), 1.22 (1.5H, d, J 6.5 Hz), 1.19 (1.5H, d, J 6.5 Hz); HPLC: [Xterra; 2.0 ml/min, methanol-10 mM aqueous ammonium acetate solution (50:50) to (80:20) over 4 min then (80:20)] 97% (1.08 min). |
| 22 | (2'S)-[1-[4-(1,2,3,3a,4,8b-hexahydro-6-methoxycyclopent-[b]indolyl)]-2-propylamine fumarate | 6-OMe (2'S) | 32% | Mixture of diastereoisomers; fumarate: NMR 400 MHz (DMSO-d$_6$) δ$_H$ 6.83 (1H, dd, J 2.5, 7.5 Hz), 6.46 (2H, s), 6.11–6.06 (1.5H, m), 6.04 (0.5H, d, J 2.5 Hz), 4.20 (1H, m), 3.68 (3H, s), 3.63 (1H, dt, J 1.5, 8 Hz), 3.44–3.11 (4H, m), 1.93 (1H, m), 1.72 (1H, m), 1.68–1.53 (3H, m), 1.40 (1H, m), 1.22 (1.5H, d,16.5 Hz), 1.19 (1.5H, d, J 6.5 Hz); HPLC: [Xterra; 2.0 ml/min, methanol-10 mM aqueous ammonium acetate solution (50:50) to (80:20) over 4 min then (80:20)] 98% (1.05 min). |

Example VI

Pharmaceutical Composition

Tablets containing the following ingredients can be manufactured in a conventional manner:

| Ingredients | Per tablet |
|---|---|
| Compound of formula I | 10.0–100.0 mg |
| Lactose | 125.0 mg |
| Maize starch | 75.0 mg |
| Talc | 4.0 mg |
| Magnesium stearate | 1.0 mg |

What is claimed is:

1. A compound selected from the group consisting of: compounds of general formula I

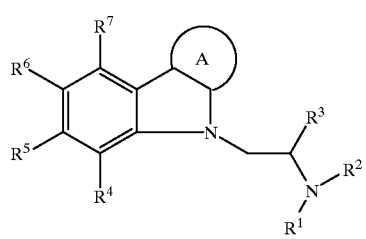

(I)

wherein $R^1$ and $R^2$ are independently selected from hydrogen, alkyl, alkenyl, alkinyl, and cycloalkyl;

$R^3$ is alkyl, alkenyl, alkinyl, or cycloalkyl;

$R^4$, $R^5$, $R^6$ and $R^7$ are independently selected from hydrogen, alkyl, alkenyl, alkinyl, cycloalkyl, halogen, haloalkyl, hydroxy, aryl, amino, mono- and dialkylamino, alkoxy, cycloalkyloxy, aryloxy, heteroaryloxy, alkylthio, alkylsulfoxyl, alkylsulfonyl, nitro, cyano, alkoxycarbonyl, aryloxycarbonyl, heteroaryloxycarbonyl, heteroaryl, alkylcarbonylamino, arylcarbonylamino, heteroarylcarbonylamino, and carboxyl;

the ring A represents a 5 or 6 membered partially unsaturated or saturated carbocyclic or saturated or partially unsaturated heterocyclic ring, wherein the two atoms of the indoline ring to which ring A is fused form a saturated C—C single bond;

pharmaceutically acceptable salts of compounds of formula I, and esters of compounds of formula I.

2. The compound according to claim 1, wherein $R^1$ and $R^2$ are independently selected from hydrogen or alkyl.

3. The compound according to claim 2, wherein $R^1$ and $R^2$ are hydrogen.

4. The compound according to claim 2, wherein $R^3$ is alkyl or cycloalkyl.

5. The compound according to claim 4, wherein $R^3$ is alkyl.

6. The compound according to claim 5, wherein $R^3$ is methyl.

7. The compound according to claim 6, wherein $R^4$, $R^6$ and $R^7$ are independently selected from hydrogen, halogen, alkyl and alkoxy.

8. The compound according to claim 7, wherein $R^4$ is hydrogen.

9. The compound according to claim 8, wherein $R^5$ is hydrogen, halogen, alkoxy, or heteroarylcarbonylamino.

10. The compound according to claim 9, wherein $R^5$ is hydrogen, chloro, methoxy, pyridylcarbonylamino or thienylcarbonylamino.

11. The compounds according to claim 10, wherein $R^5$ is hydrogen, chloro or methoxy.

12. The compound according to claim 11, wherein $R^6$ is hydrogen, halogen or alkyl.

13. The compound according to claim 12, wherein $R^6$ is hydrogen, fluoro or methyl.

14. The compound according to claim 13, wherein $R^7$ is hydrogen, halogen or alkoxy.

15. The compound according to claim 14, wherein $R^7$ is hydrogen, chloro or methoxy.

16. The compound according claim 15, wherein the ring A is a saturated carbocyclic ring.

17. The compound according to claim 16, wherein the ring A is a 5-membered ring.

18. The compound according to claim 17, wherein the ring A is cyclopentyl.

19. The compound according to claim 15, wherein the ring A is a heterocyclic ring containing a heteroatom selected from N, O, and S.

20. The compound according to claim 19, wherein the ring A is selected from the group consisting of morpholinyl, piperidinyl, tetrahydropyranyl, dihydropyranyl, tetrahydrofuranyl and dihydrofuranyl, optionally substituted with alkyl or oxo.

21. A compound selected from the group consisting of: compounds of general formula I

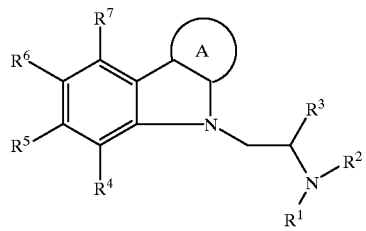

wherein
$R^1$ and $R^2$ are hydrogen or alkyl;
$R^3$ is alkyl;
$R^4$ is hydrogen;
$R^5$, $R^6$ and $R^7$ are independently selected from hydrogen, alkyl, halogen, and alkoxy;
the ring A represents a 5 or 6 membered saturated carbocyclic ring; pharmaceutically acceptable salts of compounds of formula I, and esters of compounds of formula I.

22. The compound of claim 21, wherein $R^1$ and $R^2$ are hydrogen.

23. The compound according to claim 22, selected from the group consisting of
 a) (2'S, 3aS, 8bS)-1-[4-(6-chloro-1,2,3,3a,4,8b-hexahydrocyclopent[b]indolyl]-2-propylamine,
 b) (2'S)-1-[4-(7-fluoro-6-1,2,3,3a,4,8b-hexahydro-6-methoxycycyclopent[b]indolyl)]-2-propylamine, and
 c) (2'S)-1-[4-(7-fluoro- 1,2,3,3a,4,8b-hexahydrocyclo-8-methoxypent[b]indolyl)]-2-propylamine.

24. A pharmaceutical composition comprising a compound according to claim 21 and a pharmaceutically acceptable excipient.

25. A method of treatment of diabetes mellitus, Type I diabetes, Type II diabetes, diabetes secondary to pancreatic disease, diabetes related to steroid use, Type III diabetes, hyperglycaemia, diabetic complications or insulin resistance, the method comprising administering to a patient in need of such treatment an effective dose of a compound of formula (I) as set out in claim 21.

26. A method of treatment according to claim 25 wherein said disorder is obesity.

27. A method of treatment according to claim 25, wherein said disorder is Type II diabetes.

28. A method according to claim 25, wherein said treatment is prophylactic treatment.

29. A method of treatment of obesity in a human in need of such treatment which comprises administrating to the human a therapeutically effective amount of a compound according to claim 21 and a therapeutically effective amount of a lipase inhibitor.

30. The method according to claim 29, wherein the lipase inhibitor is orlistat.

31. A method of treatment of obesity in a human in need of such treatment which comprises administrating to the human a therapeutically effective amount of a compound according to claim 21 and a therapeutically effective amount of a lipase inhibitor, wherein said lipase inhibitor is administered simultaneously, separately or sequentially.

32. A process for the preparation of a compound of formula (I)

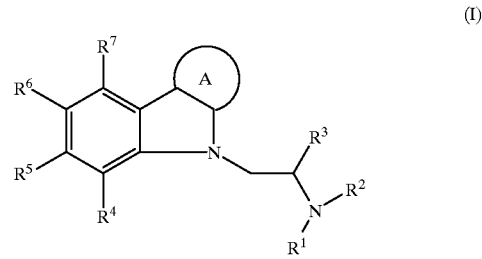

wherein
$R^1$ and $R^2$ are independently selected from hydrogen, alkyl, alkenyl, alkinyl, and cycloalkyl;
$R^3$ is alkyl alkenyl, alkinyl, or cycloalkyl;
$R^4$, $R^5$, $R^6$ and $R^7$ are independently selected from hydrogen, alkyl, alkenyl, alkinyl, cycloalkyl, halogen, haloalkyl, hydroxy, aryl, amino, mono- and dialkylamino, alkoxy, cycloalkyloxy, aryloxy, heteroaryloxy, alkylthio, alkylsulfoxyl, alkylsulfonyl, nitro, cyano, alkoxycarbonyl, aryloxycarbonyl, heteroaryloxycarbonyl, heteroaryl, alkylcarbonylamino, arylcarbonylamino, heteroarylcarbonylamino, and carboxyl;
the ring A represents a 5 or 6 membered partially unsaturated or saturated carbocyclic or saturated or partially unsaturated heterocyclic ring, wherein the two atoms of the indoline ring to which ring A is fused form a saturated C—C single bond;
the process comprising
 a) reaction of a compound of formula (IV)

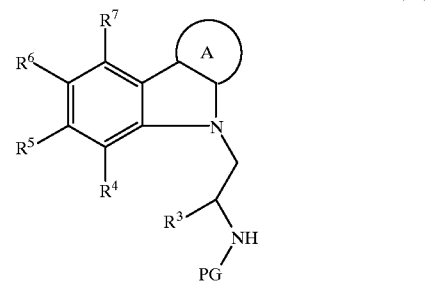

wherein $R^3$ to $R^7$ and A are as defined in claim 1 and PG is an amino-protecting group, with a reagent suitable to remove the protecting group for the preparation of compounds of formula (I) in which $R^1$ and $R^2$ are hydrogen, or
 b) for the preparation of compounds of formula (I) in which $R^1$ and $R^2$ are not hydrogen or only one of $R^1$ and $R^2$ is hydrogen, the reaction of step a), followed by reductive alkylation of a compound prepared according to step a).

* * * * *

UNITED STATES PATENT AND TRADEMARK OFFICE
CERTIFICATE OF CORRECTION

PATENT NO.     : 6,479,534 B1                                               Page 1 of 1
DATED          : November 12, 2002
INVENTOR(S)    : Jonathan Mark Bentley et al.

It is certified that error appears in the above-identified patent and that said Letters Patent is hereby corrected as shown below:

Title page,
Item [76], the inventor information is listed as "Jonathan Mark Bentley, Oakdene Court, 613 Reading Court, Winnersh, Workingham RG41 5UA (GB); James Edward Paul Davidson, Oakdene Court, 613 Reading Court, Winnersh, Workingham RG41 5UA (GB); Howard Langham Mansell, Oakdene Court, 613 Reading Court, Winnersh, Workingham RG41 5UA (GB); Nathaniel Julius Thomas Monck, Oakdene Court, 613 Reading Court, Winnersh, Workingham RG41 5UA (GB); the inventor information should read -- Jonathan Mark Bentley; James Edward Paul Davidson; Howard Langham Mansell; Nathaniel Julius Thomas Monck, all of Winnersh, Workingham (GB) --.

Insert -- [73] Hoffmann-La Roche Inc.– Nutley, New Jersey, U.S.A.
          Vernalis Research Limited –Winnersh, Workingham, England --.

After "*Assistant Examiner*" insert:
-- [74] *Attorney, Agent, or Firm*—George W. Johnston and Dennis P. Tramaloni --.

Signed and Sealed this

First Day of April, 2003

JAMES E. ROGAN
*Director of the United States Patent and Trademark Office*